US008710068B2

(12) United States Patent
Berezov et al.

(10) Patent No.: US 8,710,068 B2
(45) Date of Patent: Apr. 29, 2014

(54) METHOD OF TREATING CANCER USING A SURVIVIN INHIBITOR

(75) Inventors: Alan Berezov, West Hollywood, CA (US); Qiang Wang, North Hollywood, CA (US); Ramachandran Murali, Los Angeles, CA (US); Mark I. Greene, Penn Valley, PA (US)

(73) Assignee: The Trustees Of The University Of Pennsylvania, Philadelphia, PA (US)

( * ) Notice: Subject to any disclaimer, the term of this patent is extended or adjusted under 35 U.S.C. 154(b) by 114 days.

(21) Appl. No.: 13/142,731

(22) PCT Filed: Jan. 19, 2010

(86) PCT No.: PCT/US2010/021365
§ 371 (c)(1), (2), (4) Date: Nov. 1, 2011

(87) PCT Pub. No.: WO2010/083505
PCT Pub. Date: Jul. 22, 2010

(65) Prior Publication Data
US 2012/0122910 A1     May 17, 2012

Related U.S. Application Data

(60) Provisional application No. 61/145,664, filed on Jan. 19, 2009.

(51) Int. Cl.
*A01N 43/42* (2006.01)

(52) U.S. Cl.
USPC ........... 514/278; 514/568; 514/456; 514/418; 514/414

(58) Field of Classification Search
USPC ........................ 514/278, 568, 456, 418, 414
See application file for complete search history.

(56) References Cited

FOREIGN PATENT DOCUMENTS

| WO | WO 96/34851 | 11/1996 |
|----|----|----|
| WO | WO 00/01349 | 1/2000 |
| WO | WO 01/73014 | 10/2001 |
| WO | WO 02/02622 | 1/2002 |
| WO | WO 2006/097323 | 9/2006 |
| WO | WO2008083326 | * 7/2008 |

OTHER PUBLICATIONS

Tirado et al, Cancer Res., 2005, 65, 9320-9327.*
Chen et al, Tetrahedron, 2007, 63, 10437-10444.*
Eckelbarger et al, JACS, 2006, 128, 10370-10371.*
Pandit et al, 229th ACS National Meeting Abstracts, 2005, MED-477.*
Ainsztein et al., "INCENP centromere and spindle targeting: identification of essential conserved motifs and involvement of heterochromatin HP1", J. Cell Biol., Dec. 1998, 143(7), 1763-1774.
Altieri, "Targeted therapy by disabling crossroad signaling networks: the survivin paradigm", Mol. Cancer Ther., Mar. 2006, 5, 478-482.
Altieri, "Validating survin as a cancer therapeutic target", Nat. Rev. Cancer, Jan. 2003, 3(1), 46-54.
Asanuma et al., "Survivin expression is regulated by coexpression of human epidermal growth factor receptor 2 and epidermal growth factor receptor via phosphatidylinositol 3-kinase/AKT signaling pathway in breast cancer cells", Cancer Res., Dec. 2005, 65, 11018-11025.
Beardmore et al., "Survivin dynamics increases at centromeres during G2/M phase transition and is regulated by microtubule-attachment and Aurora B kinase activity", J. Cell Sci., Aug. 15, 2004, 117, 4033-4042.
Carvalho et al., "Survivin is required for stable checkpoint activation in taxol-treated HeLa cells", J. Cell Sci., Jul. 2003, 116, 2987-2998.
Chantalat et al., "Crystal structure of human survivin reveals a bow tie—shaped dimer with two unusual alpha-helical extensions", Mol. Cell, Jul. 2000, 6, 183-189.
Dohi et al., "Mitochondrial survivin inhibits apoptosis and promotes tumorigenesis", J. Clin. Invest., Oct. 2004, 114, 1117-1127.
Ewing et al., "DOCK 4.0: search strategies for automated molecular docking of flexible molecule databases", Comput. Aided Mol. Des., May 2001, 15(5), 411-428.
Fingl et al., "The Pharmacological Basis of Therapeutics", 1975, Chapter 1, p. 1.
Fortugno et al., "Survivin exists in immunochemically distinct subcellular pools and is involved in spindle microtubule function", J. Cell Sci., Feb. 2002, 115, 575-585.
Ghosh et al., "Activated checkpoint kinase 2 provides a survival signal for tumor cells", Cancer Res., Dec. 2006, 66(24), 11576-11579.
Giodini et al., "Regulation of microtubule stability and mitotic progression by survivin", Cancer Res., May 2002, 62, 2462-2467.
Goshima et al., "Mechanisms for focusing mitotic spindle poles by minus end-directed motor proteins", J. Cell Biol., Oct. 2005, 171, 229-240.
Goshima et al., "The roles of microtubule-based motor proteins in mitosis: comprehensive RNAi analysis in the Drosophila S2 cell line", J. Cell Biol., Sep. 2003, 162, 1003-1016.
Hansen et al., "SPC 3042: a proapoptotic survivin inhibitor", Mol. Cancer Ther., Sep. 2008, 7, 2736-3745.
International Search Report and Written Opinion of corresponding application PCT/US2010/21365, mailed Mar. 22, 2010, 14 pages.
Jeyaprakash et al., "Structure of a Survivin-Borealin-INCENP core complex reveals how chromosomal passengers travel together", Cell, Oct. 2007, 131(2), 271-285.
Jonkers and Berns, " Oncogene addiction: sometimes a temporary slavery", Cancer Cell, Dec. 2004, 6(6), 535-538.
Kappler et al., "Knockdown of survivin expression by small interfering RNA reduces the clonogenic survival of human sarcoma cell lines independently of p53", Cancer Gene Ther., Mar. 2004, 11, 186-193.

(Continued)

*Primary Examiner* — Jason M Sims
*Assistant Examiner* — Ibrahim D Bori

(57) ABSTRACT

Disclosed herein are methods of treating cancer by administering to a patient a small molecule inhibitor of Survivin. Also disclosed herein are methods of inhibiting Survivin dimerization in a patient by administering a compound of formula (I), (II), (III), or (IV). Methods of inducing cell cycle arrest in cancer cells, comprising G2/M stage arrest, in a patient by administering a compound of formula (I), (II), (III), or (IV) are also disclosed. Further disclosed herein are methods of inducing apoptosis in cancer cells in a patient by administering a compound of formula (I), (II), (III), or (IV).

13 Claims, 28 Drawing Sheets

(56) References Cited

OTHER PUBLICATIONS

Kelecom, "Synthesis marine natural products in Brazil", J. Braz. Chem. Soc., Apr. 1998, 9(2), 101-118.

Khodjakov et al., "Minus-end capture of preformed kinetochore fibres contributes to spindle morphogenesis", J. Cell Biol., Feb. 2003, 160(5), 671-683.

Kops et al., "On the road to cancer: aneuploidy and the mitotic checkpoint", Nat. Rev. Cancer, Oct. 2005, 5, 773-785.

Lens et al., "Survivin is required for a sustained spindle checkpoint arrest in response to lack of tension", Embo J., Jun. 2003, 22, 2934-2947.

Li and Ling, "Survivin study: an updated of 'what is the next wave?'", J. Cell Physiol., Sep. 2006, 208(3), 476-486.

Li et al., "Control of apoptosis and mitotic spindle checkpoint by survivin", Nature, Dec. 1998, 396, 580-584.

Li et al., "Pleiotropic cell-division defects and apoptosis induced by interference with survivin function", Nat. Cell Biol., Dec. 1999, 1, 461-466.

Liang et al., "Anatomy of protein pockets and cavities: measurement of binding site geometry and implications for ligand design", Protein Sci., Sep. 1998, 7(9), 1884-1897.

Lopez et al., "The anticancer activity of the transcription inhibitor terameprocol (meso-tetra-O-methyl nordihydroguaiaretic acid) formulated for systemic administration", Anti-cancer Drugs, Sep. 2007, 18(8), 933-939.

Maiato et al., "Kinetochore-driven formation of kinetochore fibres contributes to spindle assembly during animal mitosis", J. Cell Biol., Nov. 2004, 167(5), 831-840.

Maiato et al., "Kinetochore-microtubule interactions during cell division", Chromosome Res., 2004, 12(6), 585-597.

Murali et al., "Disabling TNF receptor signaling by induced conformation perturbation of tryptophan-107", PNAS, Aug. 2, 2005, 102(31), 10970-10975.

Musacchio and Hardwick, "The spindle checkpoint: structural insights into dynamic signaling", Nat. Rev. Mol. Cell Biol., Oct. 2002, 3, 731-741.

Nakahara et al., "YM155, a novel small-molecule survivin suppressant, induces regression of established human hormone-refractory prostate tumor xenografts", Cancer Research, Sep. 2007, 67, 8014-8021.

Nicholson, "From bench to clinic with apoptosis-based therapeutic agents", Nature, Oct. 2000, 407, 810-816.

Noton et al., "Molecular analysis of survivin isoforms: evidence that alternatively spliced variants do not play a role in mitosis", J. Biol. Chem., Jan. 2006, 281, 1286-1295.

O'Connor et al., "Regulation of apoptosis at cell division by p34cdc2 phorphorylation of survivin", PNAS, Nov. 21, 2000, 97, 13103-13107.

Pennati et al., "Targeting survivin in cancer therapy: fulfilled promises and open questions", Carcinogenesis, Mar. 2007, 28(6), 1133-1139.

Plescia et al., "Rational design of shepherdin, a novel anticancer agent", Cancer Cell, May 2005, 7, 457-468.

Ranu et al., "A task specific basic ionic liquid, (bmlm)OH-promoted efficient, green and one-pot synthesis of tetrahydrobenzo(b)pyran derivatives" Indian J. Chem., Jul. 2008, 47B, 1108-1112.

Rodel et al., "Survivin antisense oligonucleotide effectively radiosensitize colorectal cancer cells in both tissue culture and murine xenograft models", Int. J. Radiat. Oncol. Biol. Phys., May 2008, 71, 247-255.

Rosa et al., "Survivin modulates microtubule dynamics and nucleation throughout the cell cycle", Mol. Biol. Cell, Mar. 1, 2006, 17, 1483-1493.

Sampath et al., "The chromosomal passenger complex is required for chromatic-induced microtubule stabilization and spindle assembly", Cell, Jul. 23, 2004, 118(2), 187-202.

Sandall et al., "A Birl-Sil15 complex connects centromeres to microtubules and is required to sense kinetochore tension", Cell, Dec. 2006, 127(6),1179-1191.

Satoh et al., "Expression of survivin is correlated with cancer cell apoptosis and is involved in the development of human pancreatic duct cell tumors", Cancer, Jul. 2001, 92, 271-278.

Song et al., "Direct interaction between surviving and Smac//DIABLE is essential for the anti-apoptotic activity of surviving during taxol-induced apoptosis", J. Biol. Chem., Jun. 2003, 278, 23130-23140.

Sun et al., "Solution structure of human survivin and its binding interface with Smac/Diablo", Biochemistry, Jan. 2005, 44(1), 11-17.

Temme et al., "Localization, dynamics, and function of surviving revealed by expression of functional surviving DsRed fusion proteins in the living cell", Mol. Biol. Cell, Jan. 2003, 14, 78-92.

Tulu et al., "Molecular requirements for kinetochore-associated microtubule formation in mammalian cells", Curr. Biol., Mar. 2006, 16, 536-541.

Uren et al., "Survivin and the inner centromere protein INCENP show similar cell-cycle localization and gene knockout phenotype", Curr. Biol., Nov. 2000, 10, 1319-1328.

Verdecia et al., "Structure of the human anti-apoptotic protein survivin reveals a dimeric arrangement", Nat. Struct. Biol., Jul. 2000, 7, 602-608.

Vong et al., "Chromosome alignment and segregation regulated by ubiquitination of survivin", Science, Dec. 2005, 310(5753), 1499-1504.

Wang and Greene, "EGFR enhances Survivin expression through the phosphoinositide 3 (PI-3) kinase signaling pathway", Exp. Mol. Pathol., Oct. 2005, 79(2), 100-107.

Wendt et al., "Discovery of a novel small molecule binding site of human survivin", Bioorg. Med. Chem. Lett., Jun. 2007, 17(11), 3122-3129.

Wheatley et al., "Aurora B phosphorylation in vitro identifies a residue of survivin that is essential for its localization ad binding to inner centromere protein (INCENP) in vivo", J. Biol. Chem., Feb. 13, 2004, 279, 5655-5660.

Wobser et al., "Complete remission of liver metastasis of pancreatic cancer under vaccination with HLA-A2 restricted peptide derived from the universal tumor antigen survivin", Cancer Immunol. Immunother., Oct. 2006, 55(10), 1294-2198.

Xia et al., "Regulation of survivin by ErbB2 signaling: therapeutic implications for ErbB2-overexpressing breast cancers", Cancer Res., Feb. 2006, 66, 1640-1647.

\* cited by examiner

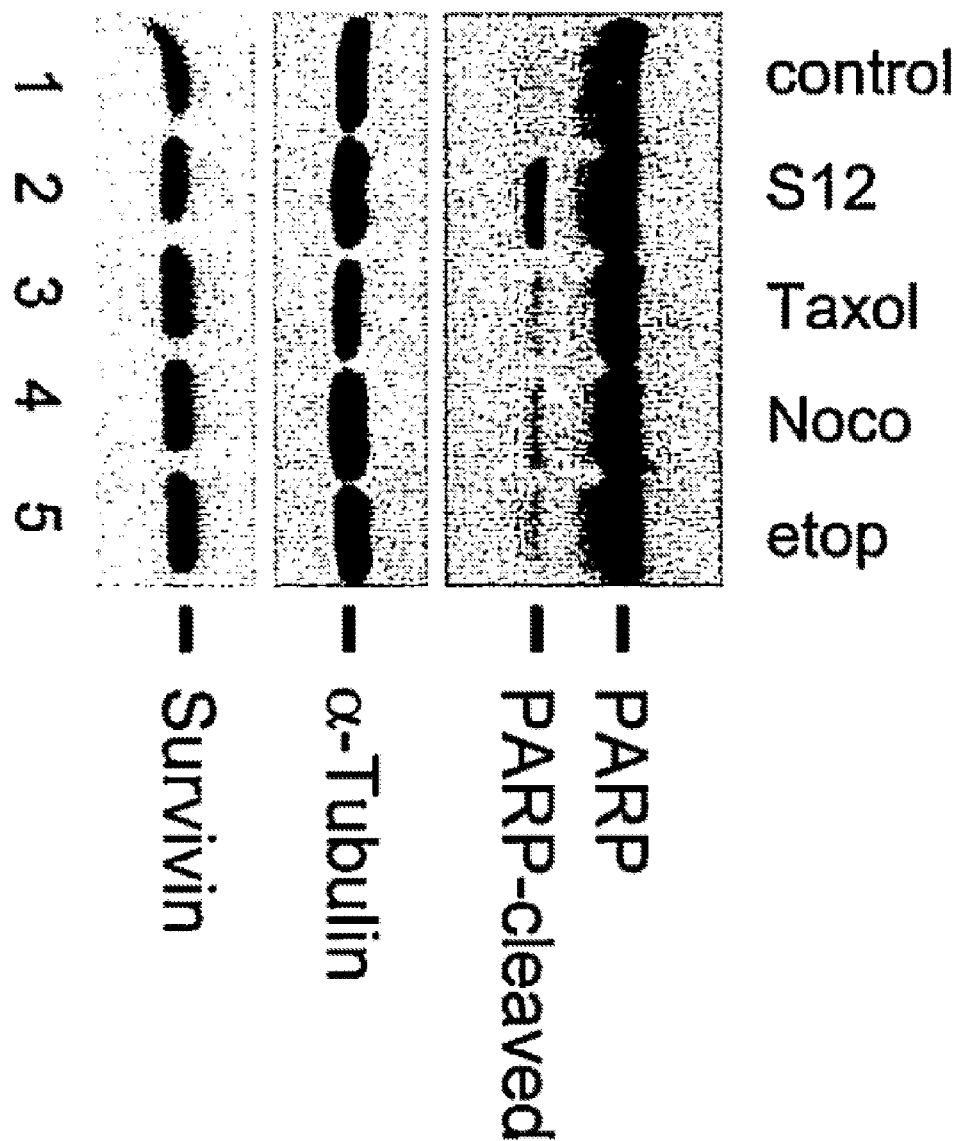

METHOD OF TREATING CANCER USING A SURVIVIN INHIBITOR

STATEMENT OF FEDERALLY SPONSORED RESEARCH

The present invention was funded by NIH grant 5R01 CA055306 from the National Cancer Institute. Pursuant to the terms of that grant, the government may have certain rights in this invention. The invention was also funded by the Breast Cancer Research Foundation and by SRA, Nidus Pharmaceuticals.

CROSS REFERENCE TO RELATED APPLICATIONS

This application is a U.S. national stage application of PCT/US2010/021365 filed on Jan. 19, 2010, which published on Jul. 22, 2010 as WO 2010/083505, and which claims priority to U.S. provisional application 61/145,664, filed Jan. 19, 2009. Each of the foregoing applications is incorporated by reference herein in its entirety.

TECHNICAL FIELD

The present invention is directed to treatments for human tumors. More particularly this invention is directed to methods of preventing and treating human cancers or tumors using small molecules having specificity for the Survivin protein.

BACKGROUND

Survivin and Cancer

Survivin is overexpressed in a large portion of human cancers. (Altieri, D. C. (2003) Validating survivin as a cancer therapeutic target. *Nat Rev Cancer* 3: 46-54; Satoh et al. (2001) Expression of survivin is correlated with cancer cell apoptosis and is involved in the development of human pancreatic duct cell tumors. *Cancer* 92:271-278). Elevated Survivin levels frequently correlate with poor prognosis. Survivin appears to have two distinct biological roles. First, Survivin exhibits anti-apoptotic activity under certain experimental conditions (Li et al. (1999) Pleiotropic cell-division defects and apoptosis induced by interference with survivin function. *Nat Cell Biol* 1:461-466; Li et al. (1998) Control of apoptosis and mitotic spindle checkpoint by survivin. *Nature* 396:580-584). Indeed, Survivin was initially identified as a member of the Inhibitor of Apoptosis (IAP) family. (Id.). Although Survivin may not function by directly binding and inhibiting caspase, as initially thought, the current data suggest that Survivin antagonizes apoptosis by acting upstream of effector caspases (Dohi et al. (2004) Mitochondrial survivin inhibits apoptosis and promotes tumorigenesis. *J. Clin Invest* 114: 1117-1127; Song et al. (2003) Direct interaction between survivin and Smac/DIABLO is essential for the anti-apoptotic activity of survivin during taxol-induced apoptosis. *J. Biol Chem* 278:23130-23140). Activation of the checkpoint kinase Chk2 by DNA damage stimulates a rapid discharge of the mitochondrial pool of Survivin in the cytosol. (Ghosh et al. (2006) Activated checkpoint kinase 2 provides a survival signal for tumor cells. *Cancer Res* 66:11476-11579). Thus, Survivin may also be involved in modulation of DNA-damage-induced apoptosis.

Secondly, more recent studies indicate that Survivin is involved in chromosome segregation during mitosis. Survivin exists in immunologically distinct pools localized in various subcellular compartments, including kinetochores and microtubules. (Fortugno et al. (2002) Survivin exists in immunochemically distinct subcellular pools and is involved in spindle microtubule function. *J. Cell Sci* 115:575-585). Of note, Survivin is a component of the chromosomal passenger protein complex, which also include Aurora kinase B, INCENP, TD-60, and Borealin. This Survivin-containing protein ensemble contributes to spindle assembly by nucleating microtubules around mitotic chromosomes. (Sampath et al. (2004) The chromosomal passenger complex is required for chromatin-induced microtubule stabilization and spindle assembly. *Cell* 118:187-202). Survivin is localized to the kinetochore following chromosome condensation and becomes relocated to the midbody after chromosome segregation and until cytokinesis (Carvalho et al. (2003) Survivin is required for stable checkpoint activation in taxol-treated HeLa cells. *J. Cell Sci* 116:2987-2988; Temme et al. (2003) Localization, dynamics, and function of survivin revealed by expression of functional survivinDsRed fusion proteins in the living cell. *Mol Biol Cell* 14:78-92; Uren et al. (2000) Survivin and the inner centromere protein INCENP show similar cell-cycle localization and gene knockout phenotype. *Curr Biol* 10:1319-1328). It has been established that Survivin plays an essential role in modulating the spindle checkpoint control, a biological mechanism that ensures accurate chromosome segregation during mitosis and thus prevents aneuploidy (Musacchio and Hardwick (2002) The spindle checkpoint: structural insights into dynamic signaling. *Nat Rev Mol Cell Biol* 3:731-741). It is postulated that overexpression of Survivin may corrupt the spindle checkpoint control and thereby contribute to chromosome instability and aneuploidy.

Survivin and the Mitotic Checkpoint

During mitosis, the spindle checkpoint monitors the integrity of the kinetochore-microtubule attachment and ensure that cells do not enter anaphase until all the chromosomes form solid attachments with microtubules (Id.). Disruption of this checkpoint is associated with loss of chromosomes or premature exit from mitosis and, consequently, aneuploidy (Kops et al. (2005) On the road to cancer: aneuploidy and the mitotic checkpoint. *Nat Rev Cancer* 5:773-785). Chromosome separation is controlled through a cascade of signaling molecules, including Mad2, Cdc20 and the APC/C protein complex. A body of evidence substantiates the role of Survivin and the other chromosome passenger proteins in regulation of the spindle checkpoint. Depletion of Survivin in mammalian cells causes abnormal chromosome alignment and high levels of aneuploidy (Lens et al. (2003) Survivin is required for a sustained spindle checkpoint arrest in response to lack of tension. *Embo J.* 22:2934-2947; Li et al. (1999) Pleiotropic cell-division defects and apoptosis induced by interference with survivin function. *Nat Cell Biol* 1:461-466; Li et al. (1998) Control of apoptosis and mitotic spindle checkpoint by survivin. *Nature* 396:580-584). In particular, loss of Survivin function abrogates a spindle checkpoint and allows re-replication of DNA without completion of cell division (Lens et al. (2003) Survivin is required for a sustained spindle checkpoint arrest in response to lack of tension. *Embo J.* 22:2934-2947). It appears that Aurora B and Mad2 are not properly localized to the kinetochore in this condition (Id.). The essential role of Survivin in cell lines is consistent with the finding that genetic targeting of Survivin in mice leads to a lethal phenotype at the early embryonic stage (Uren et al. (2000) Survivin and the inner centromere protein INCENP show similar cell-cycle localization and gene knockout phenotype. *Curr Biol* 10:1319-1328).

As a component of the chromosomal passenger complex, Survivin contributes to chromatin-associated spindle formation (Sampath et al. (2004) The chromosomal passenger complex is required for chromatin-induced microtubule stabilization and spindle assembly. *Cell* 118:187-202). This process involves the activation of Aurora kinase B, which phosphorylates the mitotic centromere-associated kinesin (MCAK) and removes its microtubule depolymerizing activity (Tulu et al. (2006) Molecular requirements for kinetochore-associated microtubule-formation in mammalian cells. *Curr Biol* 16:536-541). Survivin is phosphorylated by Aurora kinase B (Beardmore et al. (2004) Survivin dynamics increases at centromeres during G2/M phase transition and is regulated by microtubule-attachment and Aurora B kinase activity. *J. Cell Sci* 117:4033-4042; Wheatley et al. (2004) Aurora B phosphorylation in vitro identifies a residue of survivin that is essential for its localization and binding to inner centromere protein (INCENP) in vivo. *J. Biol Chem* 279:5655-5660) and sequential modifications of Survivin through ubiquitination and deubiquitination affects its localization (Vong et al. (2005) Chromosome alignment and segregation regulated by ubiquitination of survivin. *Science* 310:1499-1504). In these events, Survivin may act as a sensor of kinetochore-microtubule interaction and constitute a component of the spindle-assembly checkpoint (Sandall et al. (2006) A Bir1-Sli15 complex connects centromeres to microtubules and is required to sense kinetochore tension. *Cell* 127 1179-1191).

A fraction of Survivin directly associates with polymerized microtubules during mitosis (Alfieri (2006) Targeted therapy by disabling crossroad signaling networks: the survivin paradigm. *Mol Cancer Ther* 5:478-482). In addition, the microtubule-bound Survivin can be phosphorylated by Cdc2 during mitosis, which stabilizes the Survivin protein. Microtubule-associated Survivin contributes to proper spindle formation, by modulating microtubule dynamics through formation of a larger complex. (O'Connor et al. (2000) Regulation of apoptosis at cell division by p34cdc2 phorphorylation of survivin. *Proc Natl Acad Sci USA* 97:13103-13107; Rosa et al. (2006) Survivin modulates microtubule thermodynamics and nucleation throughout the cell cycle. *Mol Biol Cell* 17:1483-1493).

Survivin and ErbB-Mediated Transformation

Aneuploidy is a hallmark in ErbB-transformed cells and is considered as a contributing factor to development of malignancy. Our previous studies indicate that activation of EGFR leads to upregulation of Survivin (Wang and Greene (2005) EGFR enhances Survivin expression through the phosphoinositide 3 (PI-3) kinase signaling pathway. *Exp Mol Pathol* 79:100-107). Notably, modulation of Survivin levels by EGFR is dependent on the PI-3 kinase pathway but not on the MAP kinase pathway. Similarly, the signaling events initiated by ErbB2 and ErbB3 also cause increase of Survivin levels (Asanuma et al. (2005) Survivin expression is regulated by coexpression of human epidermal growth factor receptor 2 and epidermal growth factor receptor via phosphatidylinositol 3-kinase/AKT signaling pathway in breast cancer cells. *Cancer Res* 65:11018-11025; Xia et al. (2006) Regulation of survivin by ErbB2 signaling: therapeutic implications for ErbB2-overexpressing breast cancers. *Cancer Res* 66:1640-1647). Collectively, these observations raise the possibility that ErbB receptors may cause transformation by directly affecting a molecule implicated in playing a dual role in apoptosis and chromosome stability.

Cancers appear to be adapted to the transformed phenotype and become dependent on the oncogenic mutations for their maintenance and survival. This phenomenon is more recently referred to as "oncogene addiction" but this term is actually implicit to the malignant phenotype. (Joners and Berns (2004) Oncogene addiction: sometimes a temporary slavery. *Cancer cell* 6:535-538). It is possible that certain tumors, which have overexpression of Survivin and ErbB molecules, may become "addicted" to the Survivin networks. The Survivin antagonists may thus offer therapeutic benefits by targeting cancers while limiting unwanted side effects.

Survivin as a Therapeutic Target for Cancer.

Overexpression of Survivin confers on cancer cells an increase of proliferative capacity and resistance to cell death, which translates into poor clinical prognosis. In contrast, Survivin is generally not in normal tissue (Altieri, D. C. (2003) Validating survivin as a cancer therapeutic target. *Nat Rev Cancer* 3: 46-54). Combined with its roles in apoptosis and chromosome segregation during mitosis, this makes Survivin an attractive target for cancer therapy (Altieri (2003) Validating survivin as a cancer therapeutic target. *Nat Rev Cancer* 3:46-54). First, previous studies showed that disruption of Survivin in tumor cells by a genetic approach leads to immediate cell-cycle arrest and spontaneous cell death. It is conceivable that molecules that target the Survivin-containing complex may inflict potent and efficient anti-cancer effects. Secondly, one of the widely explored approaches to develop cancer therapeutics is to induce aberrant mitosis in tumors, which usually leads to cell death. For example, taxol, a compound that blocks mitosis by stabilizing tubulin polymerization and interfering with formation of the mitotic spindle, has been used to treat various forms of human cancer. Because Survivin plays an essential role in mitosis, ablation of Survivin function causes cell mitotic arrest and cell death. Thus, small molecules that target Survivin function represent a new class of agents that interfere with both apoptosis and mitosis.

To date only a small number of Survivin targeting interventions have been developed. These include molecules designed or selected to limit Survivin expression, such as an antisense molecule (LY2181308 and SPC3042) and transcriptional repressors (YM155 and EM-1421). (Rodel et al. (2008) Survivin antisense oligonucleotide effectively radiosensitize colorectal cancer cells in both tissue culture and murine xenograft models. *Int J. Radiat Oncol Biol Phys* 71:247-255; Hansen et al. (2008) SPC 3042: a proapoptotic survivin inhibitor. *Mol Cancer Ther.* 7:2736-45; Nakahara et al. (2007) YM155, a novel small-molecule survivin suppressant, induces regression of established human hormone-refractory prostate tumor xenografts. *Cancer Research* 67:8014-8021; Lopez et al. (2007) The anticancer activity of the transcription inhibitor terameprocol (meso-tetra-O-methyl nordihydroguaiaretic acid) formulated for systemic administration. *Anticancer Drugs* 18:933-939). These approaches aim to perturb Survivin expression and thereby indirectly ablate Survivin functions. Survivin peptides have also been used in vaccination protocols to generate an immune response to cancer (Wobser et al. (2006) Complete remission of liver metastasis of pancreatic cancer under vaccination with HLA-A2 restricted peptide derived from the universal tumor antigen survivin. *Cancer Immunol Immunother* 55:1294-1298). The agents that directly disrupt the physical complex between Survivin and other network components are emerging but the success remains limited. In one example, Plescia et al. developed a class of compounds that act as the combined inhibitor of Survivin and HSP90 and exhibit promising anticancer activity in vivo (Plescia et al. (2005) Rational design of shepherdin, a novel anticancer agent. *Cancer cell* 7:457-468). In another example, a number of Survivin-binding molecules have been identified in a high-throughput, affinity-based screen (Wendt et al. (2007) Discovery of a novel small molecule binding site of human survivin. *Bioorg Med Chem Lett* 17:3122-3129). However, the biological activities of these compounds have not been documented.

Survivin Protein Structure.

Survivin is a protein of 142 amino acid residues. The structure of Survivin has been determined by both crystallography (Chantalat et al. (2000) Crystal structure of human survivin reveals a bow tie-shaped dimer with two unusual alpha-helical extensions. *Mol Cell* 6:183-189; Verdecia et al. (2000) Structure of the human anti-apoptotic protein survivin reveals a dimeric arrangement. *Nat Struct Biol* 7, 602-608) and by solution NMR methods (Sun et al. (2005) Solution structure of human survivin and its binding interface with Smac/Diablo. *Biochemistry* 44:11-17). The Survivin protein forms a homodimer that resembles a "bow tie". The N-terminal region of Survivin contains a zinc-binding fold similar to the baculovirus IAP repeat (BIR) motif. This domain consists of a three-stranded β-sheet and four α-helices. The C-terminus of Survivin contains an extended α-helical coiled-coil domain. The solution NMR structure of a truncated version of the protein (1-120) unequivocally determined the dimer interface that was somewhat ambiguous in the crystal lattice (Id.).

The N-terminal region contains the structural features involved in dimerization and subcellular localization to the kinetochore and the midbody (Li and Ling (2006) Survivin study: an update of "what is the next wave"? *J. Cell Physiol* 208:476-486). In addition, mutations of the amino acid residues in this region affect the function of Survivin (Li et al. (1998) Control of apoptosis and mitotic spindle checkpoint by survivin. *Nature* 396:580-584). Notably, ubiquitination of Survivin in the N-terminal region modulates localization as well as degradation (Vong et al. (2005) Chromosome alignment and segregation regulated by ubiquitination of survivin. *Science* 310:1499-1504). A number of Survivin splice variants have been identified, such as Survivin-delta Ex3 lacking exon 3 and Survivin-2B retaining a part of intron 2 as a cryptic exon. Of note, the N-terminal region is shared by most of the variant forms (Li and Ling (2006) Survivin study: an update of "what is the next wave"? *J. Cell Physiology* 208:476-486; Noton et al. (2006) Molecular analysis of survivin isoforms: evidence that alternatively spliced variants do not play a role in mitosis. *J. Biol Chem* 281:1286-1295).

More recently, the structure of a Survivin-Borealin-IN-CENP Core Complex has been reported (Jeyaprakash et al. (2007) Structure of a Survivin-Borealin-INCENP core complex reveals how chromosomal passengers travel together. *Cell* 131:271-285). Borealin and INCENP associate with the c-terminal helical domain of Survivin to form a three-helical bundle of 1:1:1 stoichiometry. The interactions of the core components are essential for central spindle and midbody localization of the complex. Both Survivin and Borealin bind to the N terminus of INCENP (corresponding to the amino acid residues 1-58 of human INCENP), which is sufficient for targeting to the centromere (Ainsztein et al. (1998) INCENP centromere and spindle targeting: identification of essential conserved motifs and involvement of heterochromatin HP1. *J. Cell Biol* 143:1763-1774). Of note, Survivin is required for targeting of the Chromosome passenger protein complex to the centromere. There remains a need for effective therapeutics to disrupt Survivin.

Small molecules can be screened in silico to fit into the cavities on the surface of Survivin protein adjacent to the site involved in dimerization. (Wendt et al. (2007) Discovery of a novel small molecule binding site of human survivin. *Bioorganic and Medicinal Chemistry Letters* 17:3122-3129). Protein-Protein interactions can be disrupted by small molecules that lodge proximal to the interaction site (Murali et al. (2005) Disabling TNF receptor signaling by induced conformational perturbation of tryptophan-107. *Proc. Natl. Acad. Sci.* 102: 10970-75). Lodging of the small molecule into a cavity that disables the dimerization interface may lead to conformational changes that disrupt the formation of the dimer. Using this strategy, termed as "Cavity induced allosteric modification" (see WO 00/01349), we have identified an allosteric site and developed a new class of Survivin targeting small molecules by virtual screening (Ewing et al. (2001) DOCK 4.0: search strategies for automated molecular docking of flexible molecule databases. *Comput. Aided Mol. Des.* 15:411-428) that exhibit the ability to inhibit cell proliferation, block mitosis and cause tumor regression.

The currently used anti-Survivin strategies include suppressing surviving expression by antisense, ribozyme, siRNA, or shRNA approaches or antagonizing Survivin function by dominant negative Survivin. (Rosa et al. (2006) Survivin modulates microtubule dynamics and nucleation throughout the cell cycle. *Mol Biol Cell* 17:1483-1493). Recently, a small peptide, shepherdin, that blocks the interaction of heat shock protein 90 with Survivin, has been developed. (Plescia et al. (2005) Rational design of shepherdin, a novel anticancer agent. *Cancer cell* 7:457-468).

SUMMARY

The present invention generally relates to a method of treating cancer comprising administering to a patient in need thereof a small molecule inhibitor of Survivin.

In a different aspect, the invention also provides methods of inhibiting Survivin dimerization in a patient.

In yet another aspect, the invention provides a method of inducing cell cycle arrest in cancer cells, comprising G2/M stage arrest, in a patient.

The invention also features methods of inducing apoptosis in cancer cells in a patient.

The invention also features methods of inducting tumor regression in a patient.

DETAILED DESCRIPTION OF ILLUSTRATIVE EMBODIMENTS

Figure 1:
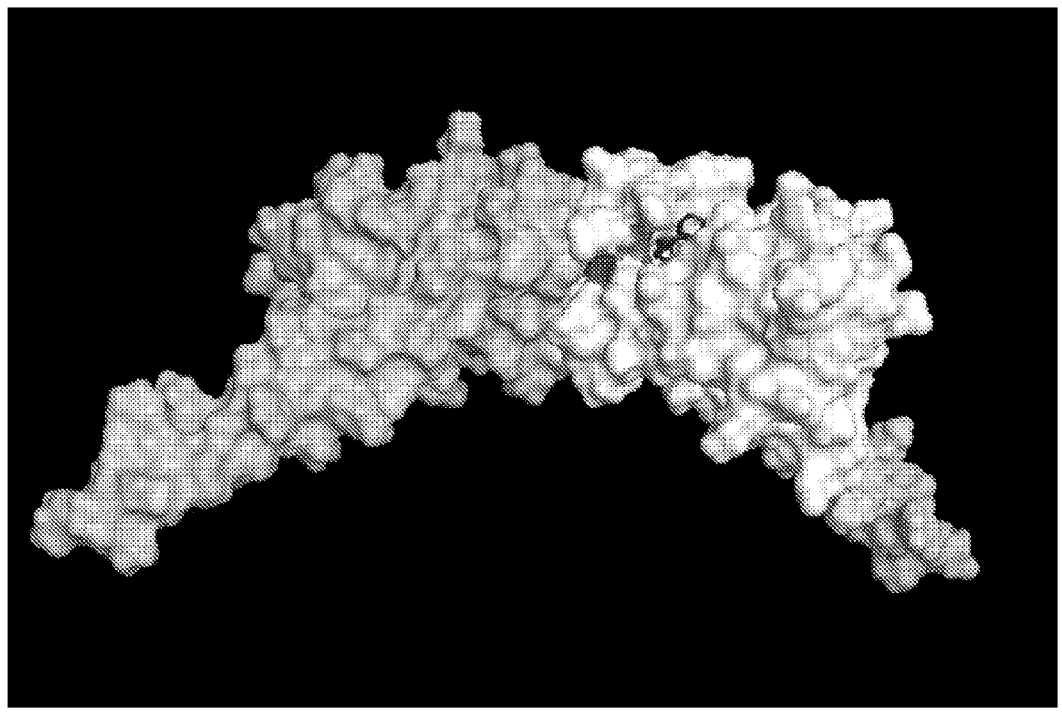
FIG. 1 illustrates the two monomers of the Survivin homodimer in cyan and white. A phenylalanine residue that makes a critical dimer interface contact is shown in red. The candidate Survivin-targeting molecules (shown in blue) have been selected using a virtual screening method to bind to a cavity located adjacent to the dimer interface. (Ewing et al. (2001) DOCK 4.0: search strategies for automated molecular docking of flexible molecule databases. *Comput. Aided Mol. Des.* 15:411-428).

The present invention generally relates to a method of treating cancer comprising administering to a patient in need thereof a small molecule inhibitor of Survivin dimerization.

We have developed small molecule inhibitors of Survivin activity that have certain advantages over other products including the ease of manufacturing and administration, the potential for oral dosing, low immunogenicity and applicability to a wider range of disease targets, including those inside the cell. The inhibitors designed in our laboratory will suppress Survivin activity by a novel, allosteric mechanism of action and are expected to overcome the limitations of the currently used anti-Survivin strategies.

Applicants have discovered a target site in a Survivin structure important for cellular functions using the CastP computer program. (Liang et al. (1998) Anatomy of protein pockets and cavities: measurement of binding site geometry and implications for ligand design. *Protein Sci.* 7:1884-1897). CastP uses weighted Delaunay triangulation and the a complex for shape measurements. It provides identification and measurements of surface accessible pockets as well as interior inaccessible cavities, for proteins and other molecules. More information is available from the CastP website (http://sts-fw.bioengr.uic.edu/castp/background.php). These molecules are selected for interactions with a cavity that is linked to the effect of Survivin dimerization. Biological assays indicate that the identified small molecule S2 and its analogs can induce sustained mitotic block and cause cell death. These effects are similar to the phenotypes resulting from ablation of Survivin with antisense or short interfering RNA. In addition, the ITC analysis confirmed that the small molecule binds to Survivin at the intended site. When administered in vivo, the Survivin-targeting molecule can inhibit tumor growth. The approach employed by applicants can thus effectively identify small molecules that disrupt Survivin functions.

Thus, in one embodiment, the invention is directed to methods of inhibiting Survivin wherein said small molecule inhibitor of Survivin is a compound of formula I or a pharmaceutical acceptable salt thereof

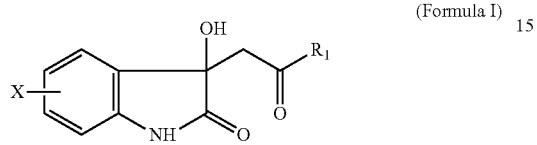
(Formula I)

wherein
X is hydrogen, halogen, —OH, alkoxy, or $C_1$-$C_4$ linear or branched alkyl; and $R_1$ is $C_1$-$C_6$ linear or branched alkyl or cycloalkyl or $C_6$-$C_{14}$ aryl optionally substituted with halogen, nitro, amine or dioxole.

Preferred examples of compounds of Formula I include the following:

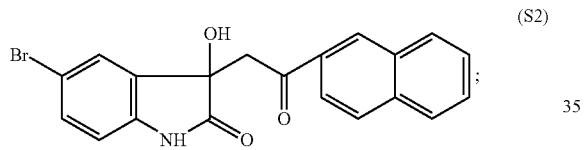
(S2)

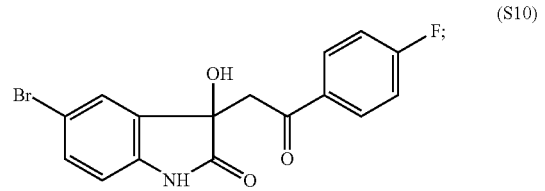
(S10)

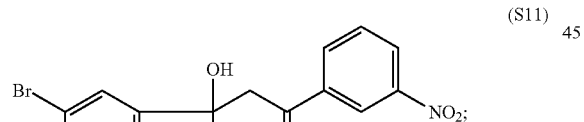
(S11)

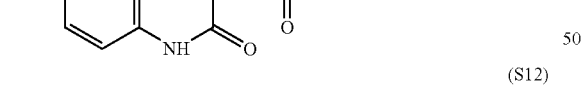
(S12)

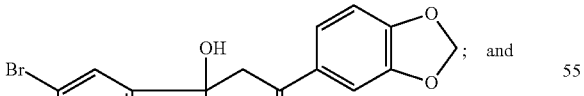
(S13) and

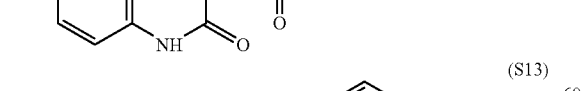

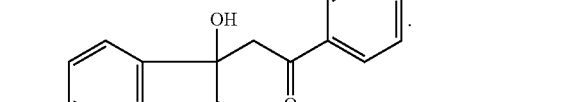

In another embodiment, the invention is directed to methods of inhibiting Survivin wherein said small molecule inhibitor of Survivin is a compound of Formula II or a pharmaceutical acceptable salt thereof:

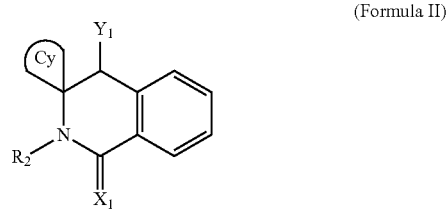
(Formula II)

wherein $R_2$ is $C_1$-$C_6$ linear or branched alkyl or cycloalkyl;

Cy is cycloalkyl;

$X_1$ is O, S, or N-alkyl; and $Y_1$ is hydrogen, carboxylic acid, thiocarboxylic acid, carboxylic acid ester, thiocarboxylic acid ester, carboxyamide, nitrile, nitro, nitroso or halogen.

Preferred examples of compounds of Formula II include:

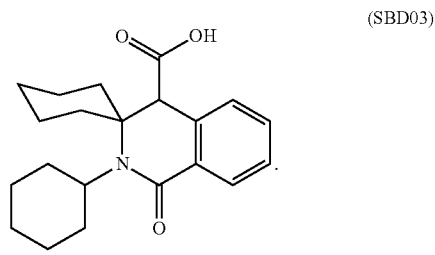 [SMILES: O=C(O)C1c2ccccc2C(=O)N(C2CCCCC2)C12CCCCC2]
(SBD03)

In yet another embodiment, the invention is directed to methods of inhibiting Survivin wherein said small molecule inhibitor of Survivin is a compound of Formula III or a pharmaceutical acceptable salt thereof:

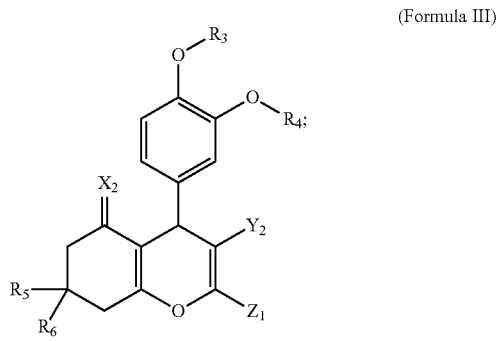
(Formula III)

wherein $X_2$ is O, S or N-alkyl;

$Y_2$ is hydrogen, nitrile, carboxylic acid, carboxylic acid ester, nitro, nitroso or halogen;

$Z_1$ is hydrogen, halogen, nitro or amine; and $R_3$, $R_4$, $R_5$ and $R_6$ are each independently $C_1$-$C_6$ linear or branched alkyl or cycloalkyl.

Preferred examples of compounds of Formula III include:

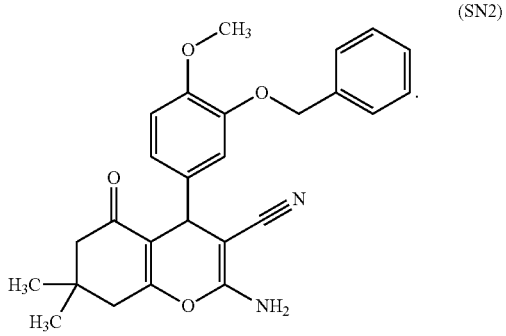 [SMILES: COc1ccc(C2C(C#N)=C(N)OC3=C2C(=O)CC(C)(C)C3)cc1OCc1ccccc1]
(SN2)

In a further embodiment, the invention is directed to methods of inhibiting Survivin wherein said small molecule inhibitor of Survivin is a compound of Formula IV or a pharmaceutical acceptable salt thereof:

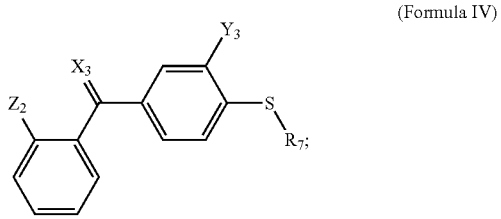
(Formula IV)

wherein $R_7$ is linear or branched alkyl or cycloalkyl;
$X_3$ is O, S or N-alkyl;
$Y_3$ is hydrogen, nitrile, carboxylic acid, carboxylic acid ester, nitro, nitroso or halogen; and
$Z_2$ is hydrogen, carboxylic acid, thiocarboxylic acid, carboxylic acid ester, thiocarboxylic acid ester, carboxy amide, nitrile, nitro, nitroso or halogen.

Preferred examples of compounds of Formula IV include:

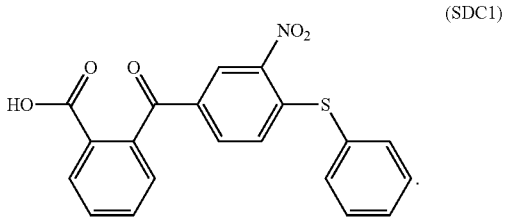 [SMILES: O=C(O)c1ccccc1C(=O)c1ccc(Sc2ccccc2)c([N+](=O)[O-])c1]
(SDC1)

In another aspect, the invention provides a method of inhibiting Survivin dimerization in a patient comprising administering to a patient in need thereof any one of the previously described compounds.

In yet another aspect, the invention provides a method of inducing cell cycle arrest in cancer cells, comprising G2/M stage arrest, in a patient comprising administering to a patient in need thereof any one of the previously described compounds.

The invention also features methods of inducing apoptosis in cancer cells in a patient comprising administering to a patient in need thereof any one of the previously described compounds.

As used herein, the term "alkyl" refers to a saturated branched or linear hydrocarbon group. Typical alkyl groups include, but are not limited to, methyl, ethyl, propyl, isopropyl, butyl, isobutyl, t-butyl, pentyl, isopentyl, hexyl and the like. In preferred embodiments, the alkyl groups are ($C_1$-$C_5$) alkyl, with ($C_1$-$C_3$) being particularly preferred.

As used herein, "substituted alkyl" refers to an alkyl group wherein one or more hydrogen atoms are each independently replaced with other substituents.

As used herein, "alkoxy" refers to RO where R is $C_1$-$C_8$ alkyl or aryl.

As used herein, the term "aryl" refers to a moiety having an unsaturated cyclic hydrocarbon group which has a conjugated (4n=2) π electron system. Typical aromatic moieties include, but are not limited to, benzene, naphthalene, anthracene, azulene, indacene and the like. In preferred embodiments, the aromatic moiety contains 5-20 carbons in the ring system, with 5-10 carbon atoms being particularly preferred.

As used herein, the term "substituted aryl" refers to an aromatic moiety wherein one or more hydrogen atoms are each independently replaced with other substituents.

As used herein, "cycloalkyl" refers to C3-C8 cycloalkyl group.

As used herein, "carboxylic acid ester" refers to C1-C8 alkyl carboxylic acid ester.

The foregoing molecules are either commercially available (for example from Maybridge) or may readily be prepared by methods known to those of skill in the art of organic chemical synthesis.

The small molecules described above target a cavity in the N-terminal region of Survivin that contains the structural features critical to dimerization and subcellular localization. (Li et al. (2006) Survivin study: an update of "what is the next wave?" *J. Cell Physiol* 208:476-486). In addition, mutations of the amino acid residues in this region affect other functions associated with Survivin. (Li et al. (1998) Control of apoptosis and mitotic spindle checkpoint by survivin. *Nature* 396: 580-584). Ubiquitination of Survivin in the N-terminal region modulates localization as well as degradation. (Vong et al. (2005) Chromosome alignment and segregation regulated by ubiquitination of survivin. *Science* 310:1499-1504). ITC analyses confirmed that the small molecules isolated in the virtual screen bind to the Survivin protein. Importantly, the mutagenesis studies corroborated the specificity of these compounds. S12 can bind to the native Survivin protein but not to the mutants that bear small structural changes in the site targeted by these molecules. This indicates that S12 can indeed associate with the Survivin protein at the intended binding site. Because the N-terminal region is shared by most of the variant forms, it is likely that these small molecules target all the Survivin variants. (Li et al. (2006) Survivin study: an update of "what is the next wave?" *J. Cell Physiol* 208:476-486; Nicholson, D. W. (2000) From bench to clinic with apoptosis-based therapeutic agents. *Nature* 407:810-816). Thus, applicants' methods of combining virtual screen and functional analyses represent a promising approach to develop therapeutic interventions that target Survivin-associated malignancy.

S2 and its analogs can disrupt proper spindle formation causing mitotic arrest. These observations are consistent with the recent findings that Survivin is involved in regulation of microtubule dynamics. (Rosa et al. (2006) Survivin modulates microtubule dynamics and nucleation throughout the cell cycle. *Mol Biol Cell* 17:1483-1493; Giodini et al. (2002) Regulation of microtubule stability and mitotic progression by survivin. *Cancer Res* 62:2462-2467). Indeed, the chromosomal passenger proteins, including Survivin, are required for microtubule stabilization and spindle assembly during mitosis. (Sampath et al. (2004) The chromosomal passenger complex is required for chromatin-induced microtubule stabilization and spindle assembly. *Cell* 118:187-202).

In cells treated with S2 or S12, multiple aster-like microtubule bundles originate from the kinetochore. In several recent studies, it was demonstrated that the kinetochore can modulate microtubule nucleation and polymerization. (Goshima et al. (2003) The roles of microtubule-based motor proteins in mitosis: comprehensive RNAi analysis in the Drosophila S2 cell line. *J. Cell Biol* 162:1003-1016; Khodjakov et al. (2003) Minus-end capture of preformed kinetochore fibres contributes to spindle morphogenesis. *J. Cell Biol* 160:671-683; Maiato et al. (2004) Kinetochore-microtubule interactions during cell division. Chromosome Res. 12:585-597). It has been proposed that the microtubule arrays formed on the kinetochore can make physical contact with the microtubule network that arises from the microtubule organizing center or MTOC and, thereby, establish the attachment of the chromosomes to the mitotic spindle. (Maiato et al. (2004) Kinetochore-driven formation of kinetochore fibres contributes to spindle assembly during animal mitosis. *J. Cell Biol* 167:831-840; Goshima et al. (2005) Mechanism for focusing mitotic spindle poles by minus end-directed motor proteins. *J. Cell Biol* 171:229-240). Applicants' immunofluorescence study clearly showed that S2 can block extension of microtubule formation from the MTOC and the kinetochore. Moreover, the chromosomes were not properly aligned at the metaphase plate, indicating S2 perturbed the microtubule dynamics and prevented the attachment of the chromosomes to the spindle.

We have demonstrated that the anti-proliferation effects of S12 are the consequence of inhibition of mitosis, rather than general toxicity. First, the cell death caused by both S2 and S12 accompanies mitotic arrest and cells blocked in S phase are resistant to the treatment. Applicants' data support the notion that the pro-apoptotic effect of the Survivin molecules is cell cycle specific and accompanies mitotic arrest. Secondly, these two compounds do not affect other biological processes, such as DNA synthesis. The current data confirmed the anticipation that the compounds specifically target a mitotic checkpoint in dividing cells.

Survivin targeting molecules of the invention inhibit cell proliferation independent of p53 status. This is consistent with previous observations that ablation of Survivin by siRNA can block cell proliferation in both p53-positive and p53-negative cells. (Kapler et al. (2004) Knockdown of survivin expression by small interfering RNA reduces the clonogenic survival of human sarcoma cell lines independently of p53. *Cancer Gene Ther* 11:186-193). Thus, Survivin targeting therapeutics may be useful to treat cancer despite p53 mutations, which are frequently found associated with malignancy.

When tested as an anticancer agent in an in vivo tumor model, the Survivin targeting molecule S12 effectively inhibits tumor growth and appears to be well tolerated, causing no systemic toxicity after prolonged treatment. Thus, targeting the N-terminus of the Survivin protein can be used as a general strategy to treat human cancers.

As discussed above, the molecules of the invention are allosteric inhibitors of Survivin dimerization. The downstream effects of the inhibition of Survivin dimerization lead to the inhibition of cell proliferation.

Other aspects of the invention are directed to the treatment of several types of cancer. Cancers that may be treated with the Survivin targeting molecules of the invention include all solid cancers and lymphomas, particularly skin cancer, bladder cancer, breast cancer, uterine cancer, ovarian cancer, prostate cancer, lung cancer, colon cancer, pancreatic cancer, renal cancer, gastric cancer, and the like.

In another embodiment of the invention, the Survivin targeting molecules of the invention are used therapeutically in combination with one or more chemotherapeutic agents. Examples of such chemotherapeutic agents are those selected from daunorubicin, prednisone, dexamethasone, decadron, altretamine, amifostine, aminoglutethimide, dactinomycin, anastrozole, asparaginase, bicalutamide, bleomycin, busulfan, carmustine, chlorambucil, chlorodeoxyadenosine, cytosine arabinoside, estramustine, diethylstilbestrol, fludarabine, flutamide, 5-fluorouracil, goserelin, idarubicin, irinotecan, levamisol, lomustine, mechlorathamine, alkeran, mercaptopurine, carboplatin, cisplatin, paclitaxel (taxol), vinorelbine, gemcitabine, irinotecan, docetaxel, doxorubicin, epirubicin, dacarbazine, rituximab, or a rituximab-containing combination therapy selected from R-ICE (consisting of rituximab, ifosfamide, carboplatin and etoposide), or R-DHAP (consisting of rituximab, cytarabine (ara-C) and cisplatin).

Formulation and Route of Administration

The compounds of the invention may be administered to a subject per se or in the form of a pharmaceutical composition. Pharmaceutical compositions comprising the compounds of the invention may be manufactured by means of conventional mixing, dissolving, granulating, dragee-making, levigating, emulsifying, encapsulating, entrapping or lyophilizing processes. Pharmaceutical compositions may be formulated in conventional manner using one or more physiological acceptable carriers, diluents, excipients, or auxiliaries which facilitate processing of the active peptides or peptide analogues into preparations which can be used pharmaceutically. Proper formulation is dependent upon the route of administration chosen.

For topical administration the compounds of the invention may be formulated as solutions, gels, ointments, creams, suspensions etc. as are well-known in the art.

Systemic formulations include those designed for administration by injection, e.g. subcutaneous, intravenous, intramuscular, intrathecal or intraperitoneal injection, as well as those designed for transdermal, transmucosal, oral or pulmonary administration.

For injection, the compounds of the invention may be formulated in aqueous solutions, preferably in physiologically compatible buffers such as Hank's solution, Ringer's solution, or physiological saline buffer. The solution may contain formulatory agents such as suspending, stabilizing and/or dispersing agents.

Alternatively, the compounds may be in powder form for constitution with a suitable vehicle, e.g., sterile pyrogen-free water, before use.

For transmucosal administration, penetrants appropriate to the barrier to be permeated are used in the formulation. Such penetrants are generally known in the art.

For oral administration, the compounds can be readily formulated by combining the active peptides or peptide analogues with pharmaceutically acceptable carriers well known in the art. Such carriers enable the compounds of the invention to be formulated as tablets, pills, dragees, capsules, liquid gels, syrups, slurries, suspensions and the like, for oral ingestion by a patient to be treated. For oral solid formulations such as, for example, powders, capsules and tablets, suitable excipients include fillers such as sugars, such as lactose, sucrose, mannitol and sorbitol; cellulose preparations such as maize starch, wheat starch, rice starch, potato starch, gelatin, gum tragacanth, methyl cellulose, hydroxypropylmethyl-cellulose, sodium, carboxymethylcellulose, and/or polyvinylpyrrolidone (PVP); granulating agents; and binding agents. If desired, disintegrating agents may be added, such as the cross-linked polyvinylpyrrolidine, atgar, or alginic acid or a salt thereof such as sodium alginate.

If desired, solid dosage forms may be sugar-coated or enteric-coated using standard techniques.

For oral preparations such as, for example, suspensions, elixirs and solutions, suitable carriers, excipients or diluents include water, glycols, oils, alcohols, etc. Additionally, flavoring agents, preservatives, coloring agents and the like may be added.

For buccal administration, the compounds may take the form of tablets, lozenges, etc. formulated in conventional manner.

For administration by inhalation, the compounds for use according to the present invention are conveniently delivered in the form of an aerosol spray from pressurized packs or a nebulizer, with the use of a suitable propellant, e.g., dichlorodifluoromethane, trichlorofluoromethane, dichlorotetrafluoroethane, carbon dioxide, or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and suitable powder base such as lactose or starch.

The compounds may also be formulated in rectal or vaginal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example, as an emulsion in an acceptable oil) or ion exchange resins, or as sparingly soluble derivatives, for example, as a sparingly soluble salt.

Alternatively, other pharmaceutical delivery system may be employed. Liposomes and emulsions are well known examples of delivery vehicles that may be used to deliver peptides and peptide analogues of the invention. Certain organic solvents such as dimethylsulfoxide also may be employed, although usually at the cost of greater toxicity. Additionally, the compounds may be delivered using a sustained-release system, such as semipermeable matrices of solid polymers containing the therapeutic agent. Various of sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

As the compounds of the invention may contain charged side chains or termini, they may be included in any of the above-described formulations as the free acids or bases or as pharmaceutically acceptable salts. Pharmaceutically acceptable salts are those salts which substantially retain the antimicrobial activity of the free bases and which are prepared by reaction with inorganic acids. Pharmaceutical salts tend to be more soluble in aqueous and other protic solvents than are the corresponding free base forms.

Effective Dosages.

The compounds of the invention will generally be used in an amount effective to achieve the intended purpose. For use to treat or prevent cancer, the compounds of the invention, or pharmaceutical compositions thereof, are administered or applied in a therapeutically effective amount. By therapeutically effective amount is meant an amount which is effective to ameliorate, or prevent the symptoms of the disease or disorder, or prolong the survival of the patient being treated. Determination of a therapeutically effective amount is well within the capabilities of those skilled in the art, especially in light of the detailed disclosure provided herein.

For systemic administration, a therapeutically effective dose can be estimated initially from in vitro assays. For example, a dose can be formulated in animal models to achieve a circulating concentration range that includes the IC50 as determined in cell culture (i.e. the concentration of test compound that inhibits 50% of Survivin dimerization). Such information can be used to more accurately determine useful doses in humans.

Initial dosages can also be estimated from in vivo data. e.g. animal models, using techniques that are well known in the art. One having ordinary skill in the art could readily optimize administration to humans based on animal data.

Dosage amount and interval may be adjusted individually to provide plasma levels of the compounds which are sufficient to maintain therapeutic effect. Usual patient dosages for administration by injection range from about 0.1 to 5 mg/kg/day, preferably from about 0.5 to 1 mg/kg/day. Therapeutically effective serum levels may be achieved by administering multiple doses each day.

In cases of local administration or selective uptake, the effective local concentration of the compounds may not be related to plasma concentration. One having skill in the art will be able to optimize therapeutically effective local dosages without undue experimentation.

The amount of compound administered will, of course, be dependent on the subject being treated, on the subject's weight, the severity of the affliction, the manner of administration and the judgment of the prescribing physician.

Toxicity

Preferably, a therapeutically effective dose of the compound described herein will provide therapeutic benefit without causing substantial toxicity.

Toxicity of the compounds described herein can be determined by standard pharmaceutical procedures in cell cultures or experimental animals, e.g., by determining the $LD_{50}$ (the dose lethal to 50% of the population) or the $LD_{100}$ (the dose lethal to 100% of the population). The dose ratio between toxic and therapeutic effect is the therapeutic index. Compounds which exhibit high therapeutic indices are preferred. The data obtained from these cell culture assays and animal studies can be used in formulation of a dosage range that is not toxic for use in humans. The dosage of the compounds described herein lies preferably within a range of circulating concentrations that include the effective dose with little or not toxicity. The dosage may vary within this range depending on the dosage form employed and the route of administration utilized. The exact formulation, route of administration and dosage can be chosen by the individual physician in view of the patient's condition. (See, e.g., Fingl et al., In: The Pharmacological Basis of Therapeutics, Ch. 1, p. 1, 1975).

The invention having been described, the following examples are offered by way of illustration and not limitation.

EXAMPLES

1. Identification of Small Molecules that Bind Survivin and Affect its Function

Figure 2:
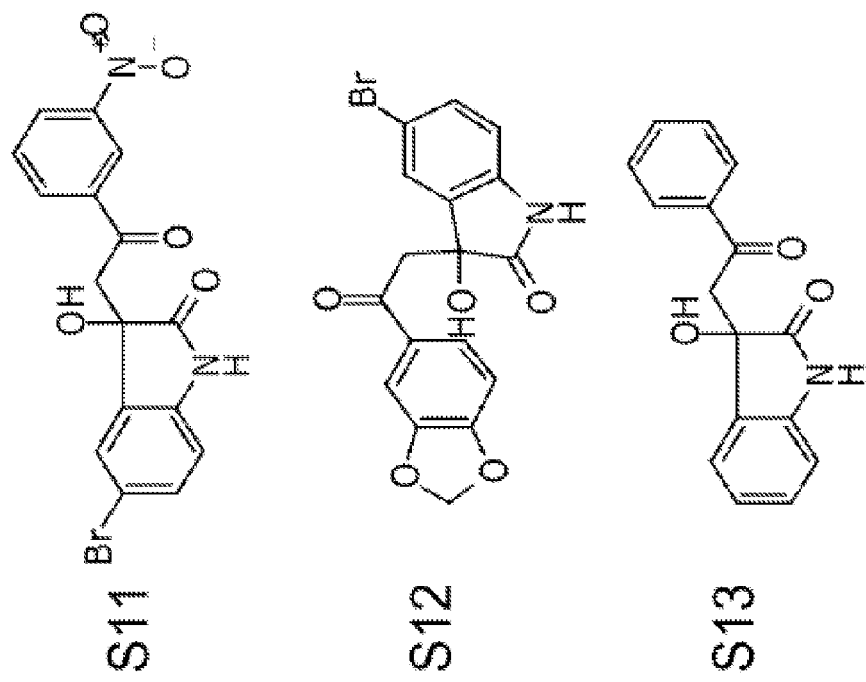
FIG. 2 illustrates the molecular structures of the pseudo-allosteric inhibitors of Survivin. S2 (5-bromo-3-hydroxy-[-2-(2-naphthyl)-2-oxoethyl]indolin-2-one) and its analogs S10, S11, S12 and S13. These molecules were selected from the Maybridge Screening Collection Database using a virtual screening method. (Ewing et al. (2001) DOCK 4.0: search strategies for automated molecular docking of flexible molecule databases. *Comput. Aided Mol. Des.* 15:411-428).
Figure 2:
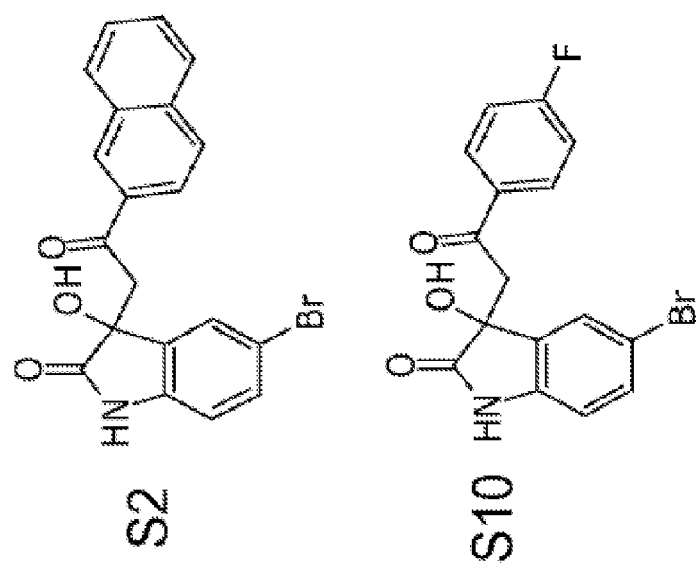

The Survivin protein forms a homodimeric state that is required to be functionally active. We predict that a small molecule capable of affecting dimerization of Survivin could have an inhibitory effect on its function. We used virtual screening to identify an allosteric cavity close to the dimerization interface (FIG. 1). (Ewing et al. (2001) DOCK 4.0: search strategies for automated molecular docking of flexible molecule databases. *Comput. Aided Mol. Des.* 15:411-428). Virtual screening of commercial small molecule databases identified a series of compounds with potential to bind to the allosteric cavity and induce a conformational change that disables the dimer. Several of the compounds (obtained from the Maybridge Screening Collection Database) were tested for binding to Survivin and for their anti-tumor activity, such as S2 and its analogs S10, S11, S12 and S13. Their molecular structures are shown in FIG. 2. These molecules are small heterocyclic ring structures that have the potential for further synthetic elaboration and modification.

2. Inhibition of Tumor Cell Proliferation

Figure 3A:
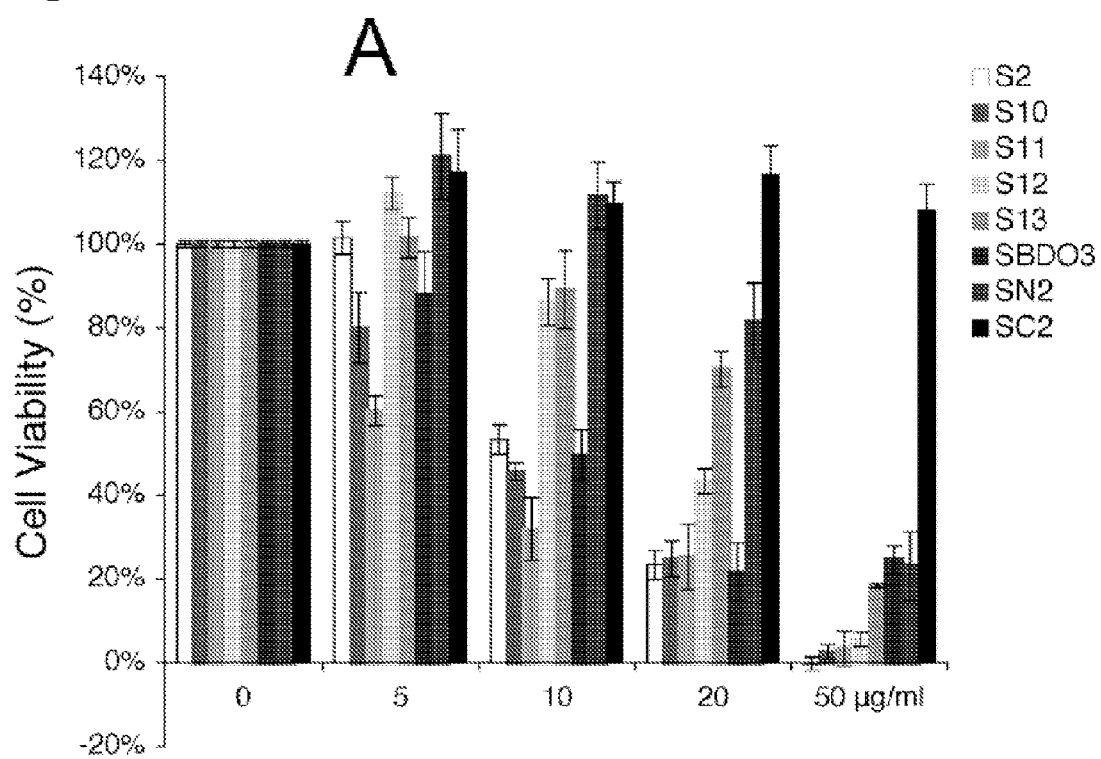
FIG. 3 illustrates the effect of S2 and its analogs on tumor cell proliferation. Cells were treated with DMSO or Survivin targeting molecules at the indicated concentration for 48 hours. The percentage of viable cells was evaluated by MTT assay. (A) AsPC1; (B) HeLa; (C) SKBR3; (D) DAOY.
Figure 3B:
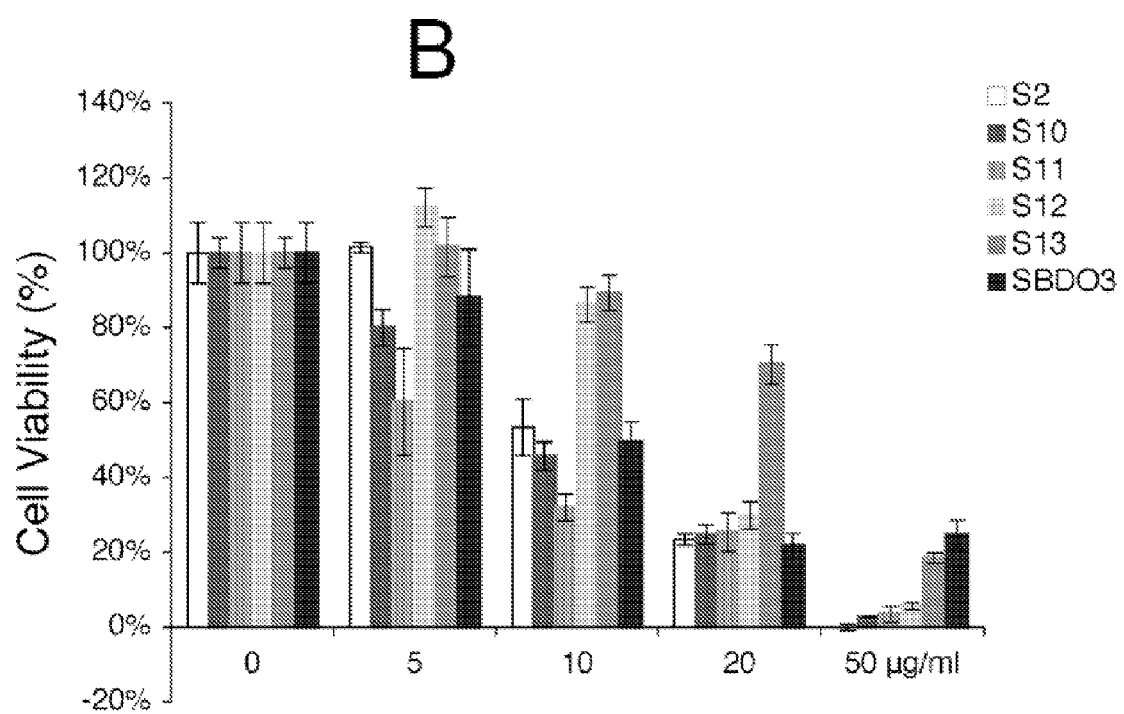
Figure 3C:
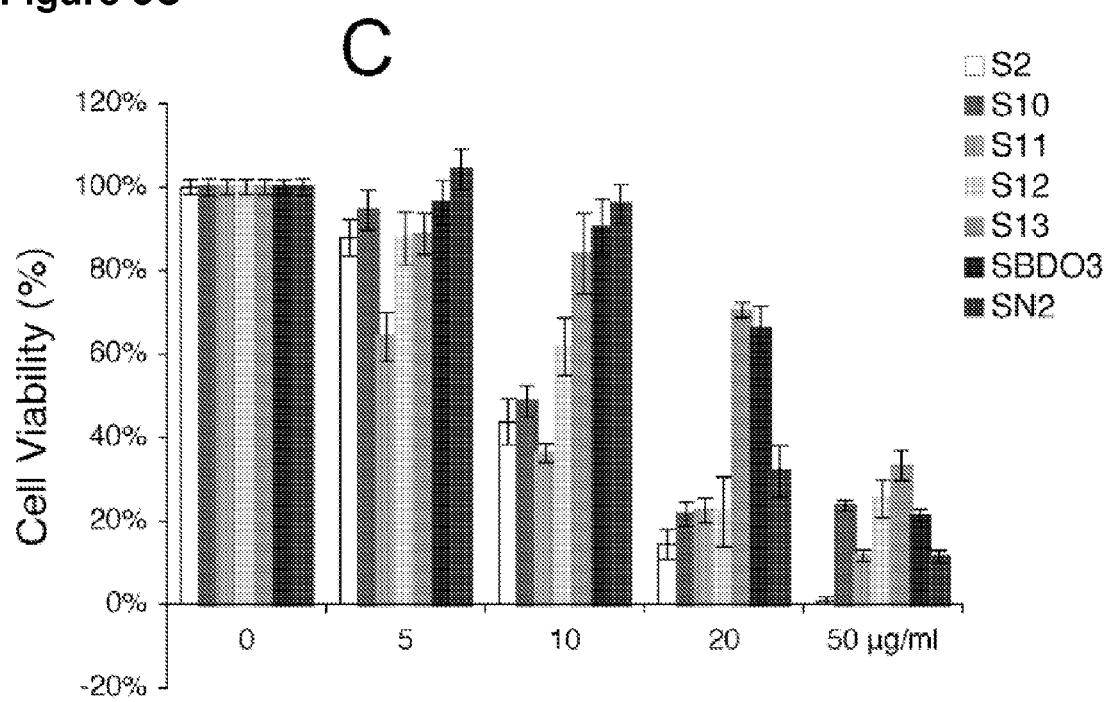
Figure 3D:
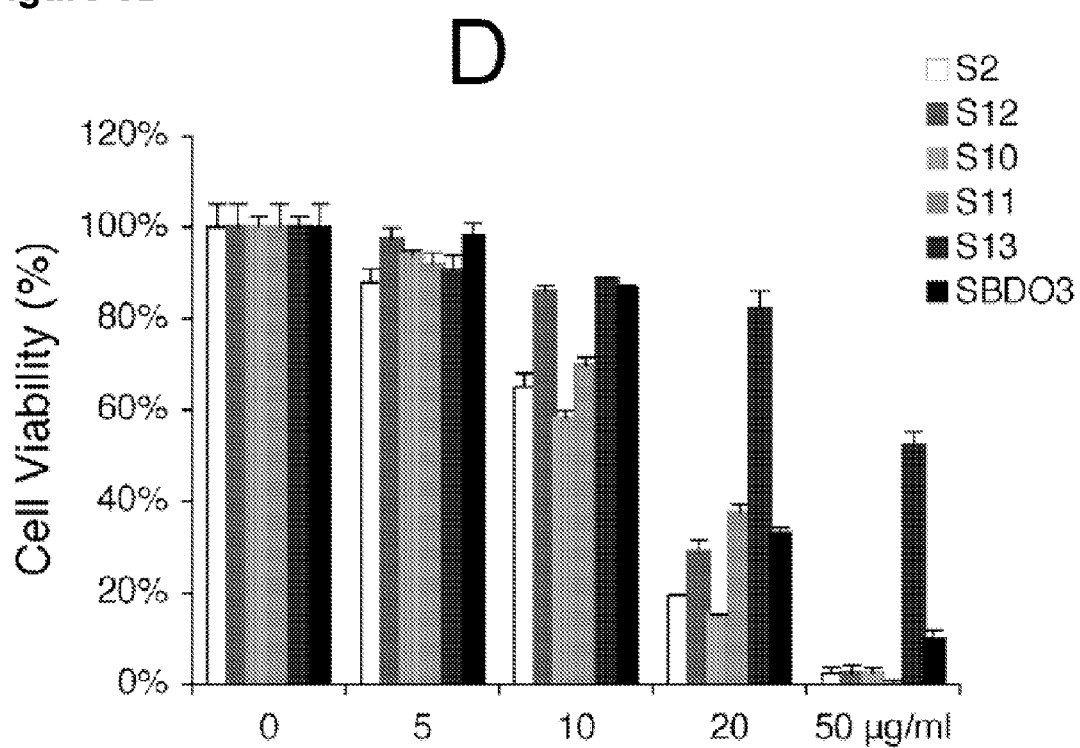

S2 and its analogs (S10, S11, S12, and S13) were tested for the ability to inhibit tumor cell proliferation by MTT assay. The AsPC1 pancreatic cancer cells were treated with DMSO, a control molecule SC2, or the Survivin-targeting compounds at the concentration of 5, 10, 20, or 50 μg/ml for 48 hours. The number of viable cells was evaluated by MTT. The data show that the Survivin-targeting compounds can inhibit cell proliferation and reduce cell viability in a dose-dependent manner (FIG. 3A). Similarly, the Survivin antagonists can inhibit proliferation of a variety of other human cancer cells, including HeLa cervical cancer cell (FIG. 3B), SKBR3 breast cancer cell (FIG. 3C), and DAOY medulloblastoma cell (FIG. 3D).

Figure 4:
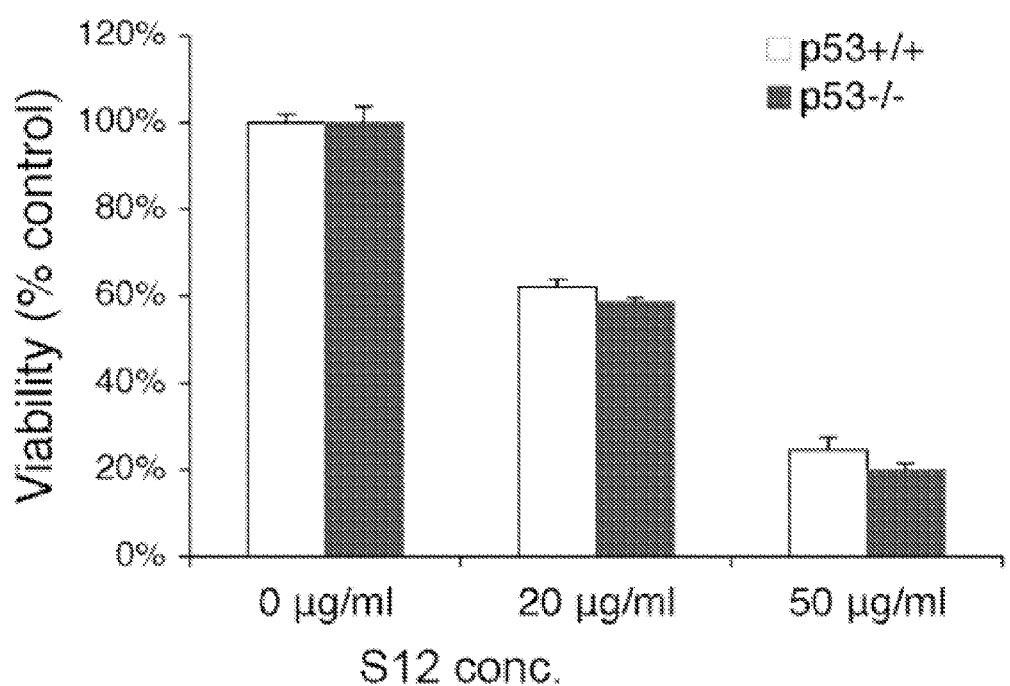
FIG. 4 illustrates the effects of S12 on proliferation of p53-positive and p53-negative cancer cells. (A) HCT116 (p53+/+) or HCT116(p53−/−) cells were treated with DMSO or S12 at the indicated concentrations for 48 hours. The percentage of viable cells was evaluated by MTT assay.

S12 is equally effective at reducing cell viability in either p53+/+ or p53−/− HCT116 cells (FIG. 4). Thus, inhibition of cell proliferation by S12 is independent of p53 status.

3. Analysis of the Binding Site of S12 in the Survivin Protein

Figure 5:
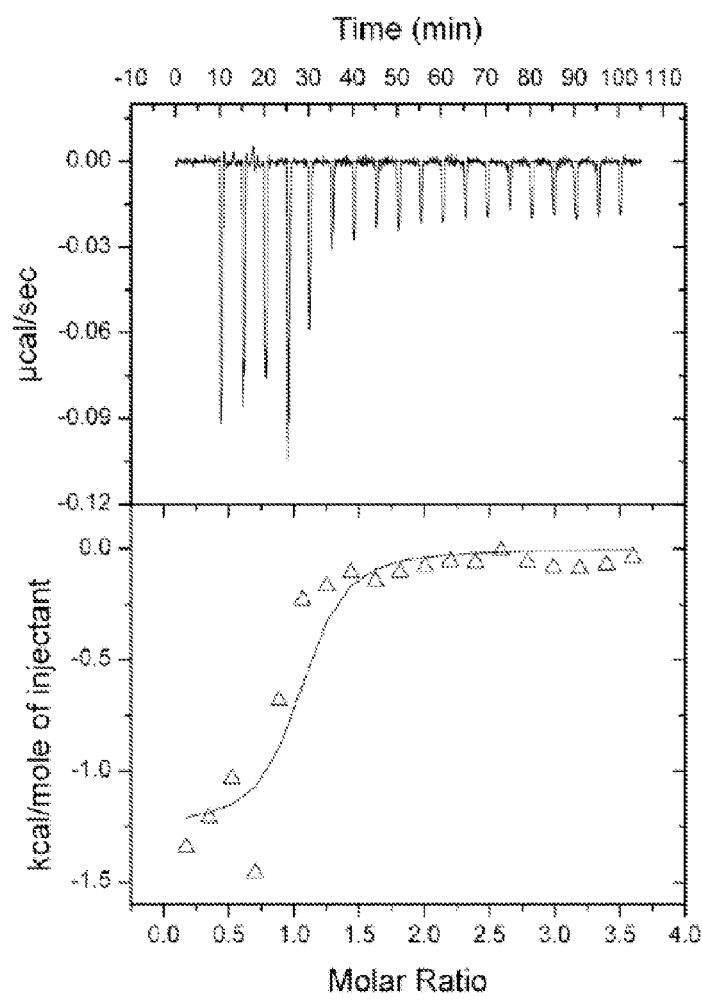
FIG. 5 illustrates an analysis of S12-Survivin binding with isothermal titration calorimetry (ITC). Single-site point mutagenesis was performed to create the Survivin mutants F86A and V89Y. The native and the mutant proteins were produced and purified from bacteria. Note that the two mutant forms of Survivin did not bind to S12 in ITC assays.
Figure 5:
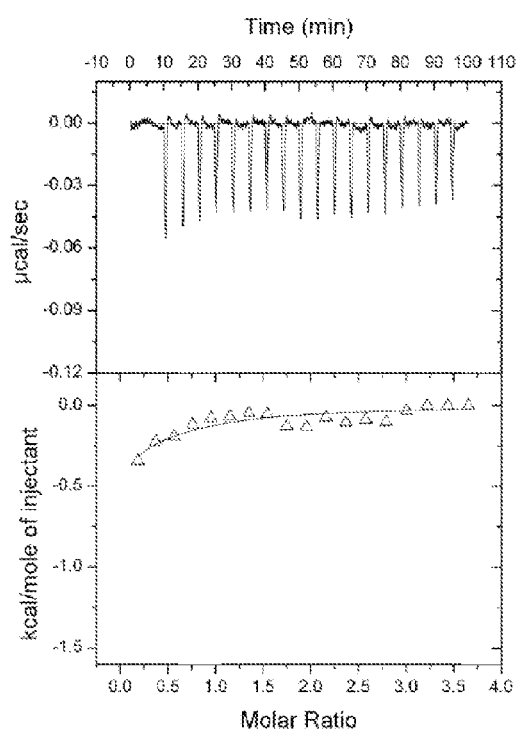
Figure 5:
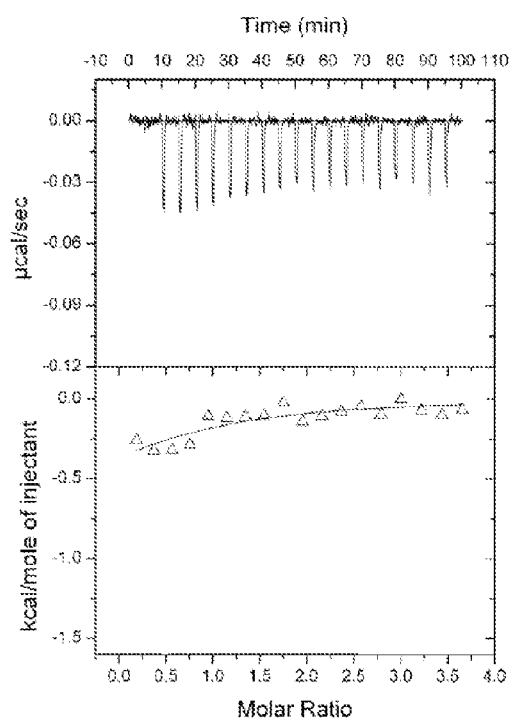

We demonstrated that S12 can bind to the Survivin protein using isothermal titration calorimetry (ITC) assays (FIG. 5; N=1.00; K=4.47±3.65×10$^6$ M$^{-1}$). In order to examine the specificity of the binding, we generated point mutations on the Survivin protein at the site presumably targeted by S12. The two mutations were substitutions of phenylalanine 86 with alanine (F86A) and valine 89 with tyrosine (V89Y). These two altered sites are also adjacent to the interface involved in dimerization of the Survivin protein. Based on structural analyses, we predict that alterations of either of these two amino acid residues may abolish the binding of S12 without affecting the overall structure of the Survivin protein. Our ITC analyses showed that, in contrast to the Survivin protein, the mutants Sur-F86A and Sur-V89Y did not bind to the Survivin targeting compound S12 (FIG. 5).

Figure 6:
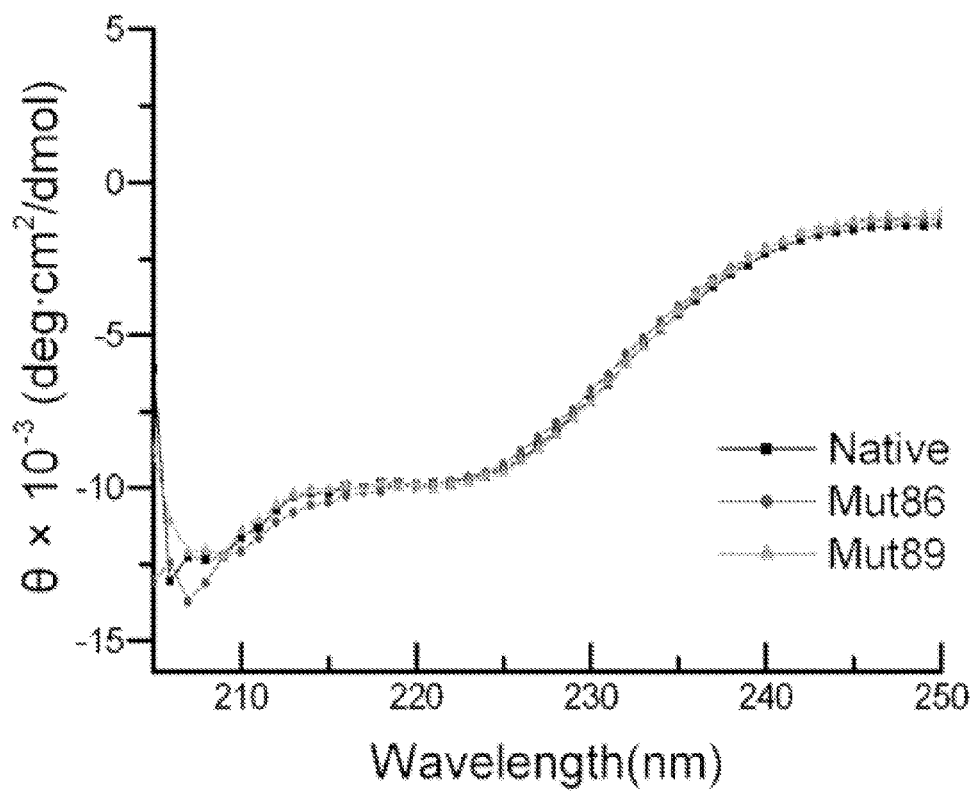
FIG. 6 illustrates the circular dichroism (CD) spectra of native and mutant Survivin protein. Mut 86: Sur(F86A); Mut89: Sur(V89Y).

To rule out the possibility that the mutations abolished binding to S12 as a result of protein misfolding, we used circular dichroism (CD) spectroscopy to analyze the global structural features of the Survivin mutant proteins. Consistent with our prediction, the CD spectra of the mutant proteins matched well with that of the native protein (FIG. 6), indicating that Sur(F86A) and Sur(V89Y) were properly folded and that no global structural changes occurred as a consequence of the mutagenesis. These studies indicate that we have identified a critical Survivin site that interacts with several small molecules.

We also investigated whether the mutation of F86A or V89Y disrupts the localization and the functions of the Survivin protein in the cell. The HA-tagged Survivin F86A and V89Y species were expressed in U2OS cells. We found that the mutations did not change the normal localization of Survivin to the midbody or the kinetochore. The cells transfected with the mutant Survivin were phenotypically indistinguishable from those with the wild-type protein. These observations indicate that the structural alterations caused by the mutagenesis were subtle and probably did not affect the function of the protein.

In summary, these results indicate that S12 can bind the native Survivin protein but not the mutants that bear small structural changes in the site targeted by the small molecules. These results indicate that S12 can indeed associate with the Survivin protein at the intended binding site adjacent to the dimerization interface.

Figure 7:
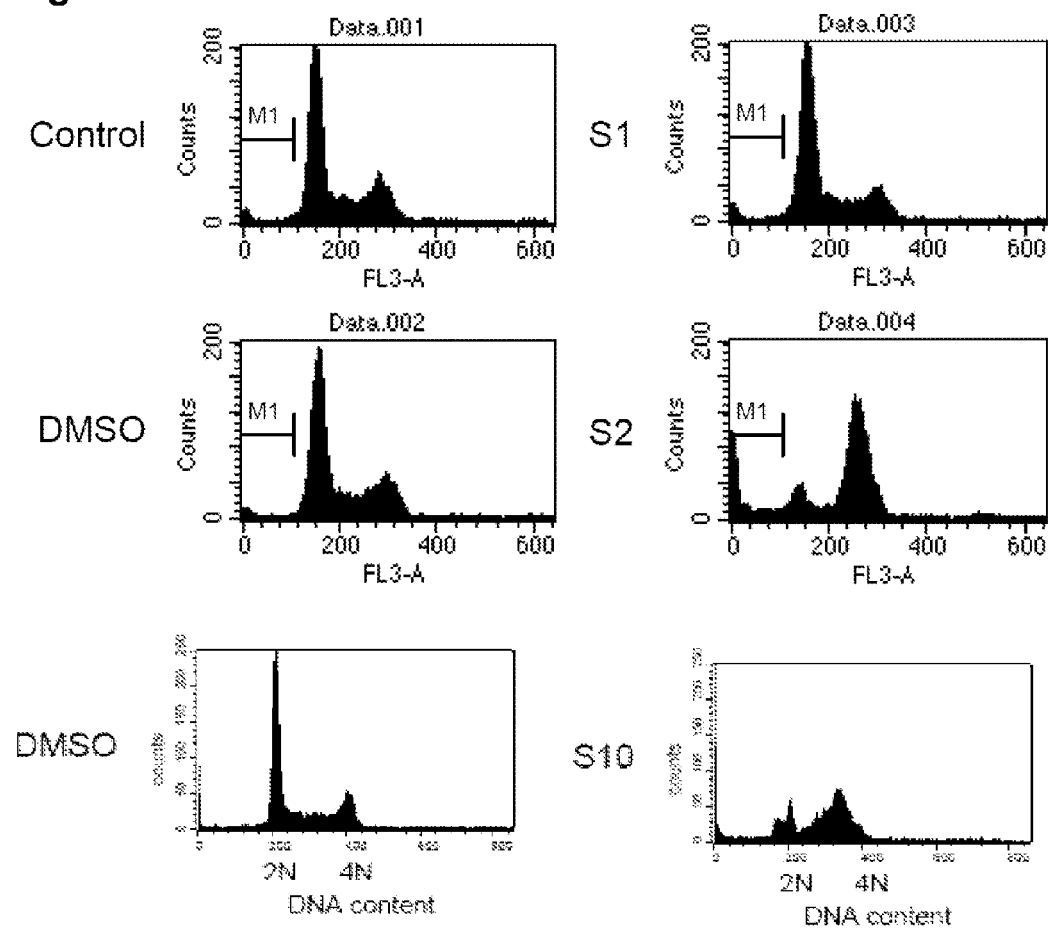
FIG. 7 illustrates the effect of S2 or S12 on cell cycle progression. HeLa cells were treated with S2, S12, S10, S1 (control compound), or DMSO (control), propidium iodide (PI) staining and FACS analysis were performed to quantify the DNA content of cells.
Figure 9A:
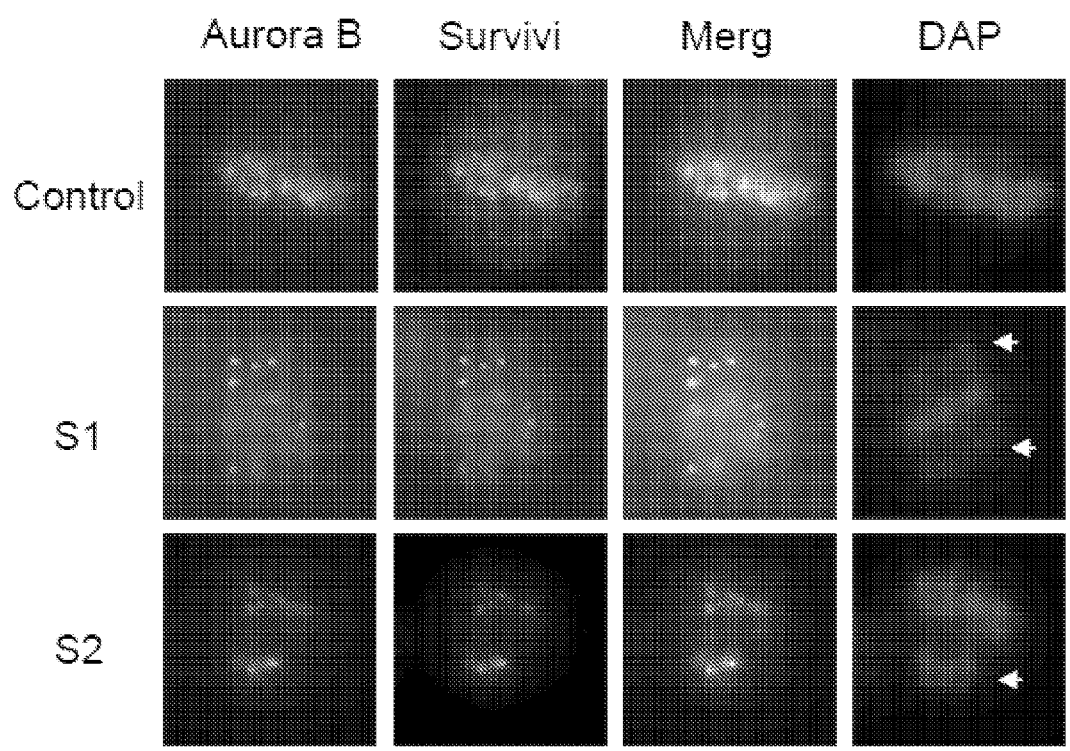
FIG. 9 illustrates the effect of S12 on mitosis. (A) HeLa cells were treated with S12, S2 or DMSO for 15 hours. The cells were then fixed and subjected to immunostaining using antibodies specific for Aurora B (green) and Survivin (red). DNA was stained with DAPI. Chromosome misalignment is indicated with the arrowheads. (B) Percentage of S12-treated cells in mitosis, in metaphase, in anaphase/telophase, or with misaligned chromosomes. (C) Percentage of S2-treated cells in mitosis, in metaphase, in anaphase/telophase, or with misaligned chromosomes. (D) HeLa cells were treated with S12 (10 μg/ml) or DMSO (control) for 15 hours. Cells were examined by PI staining of DNA content by FACS analysis. Note that the cells treated with S12 demonstrated an increase in G2/M population.
Figure 9:
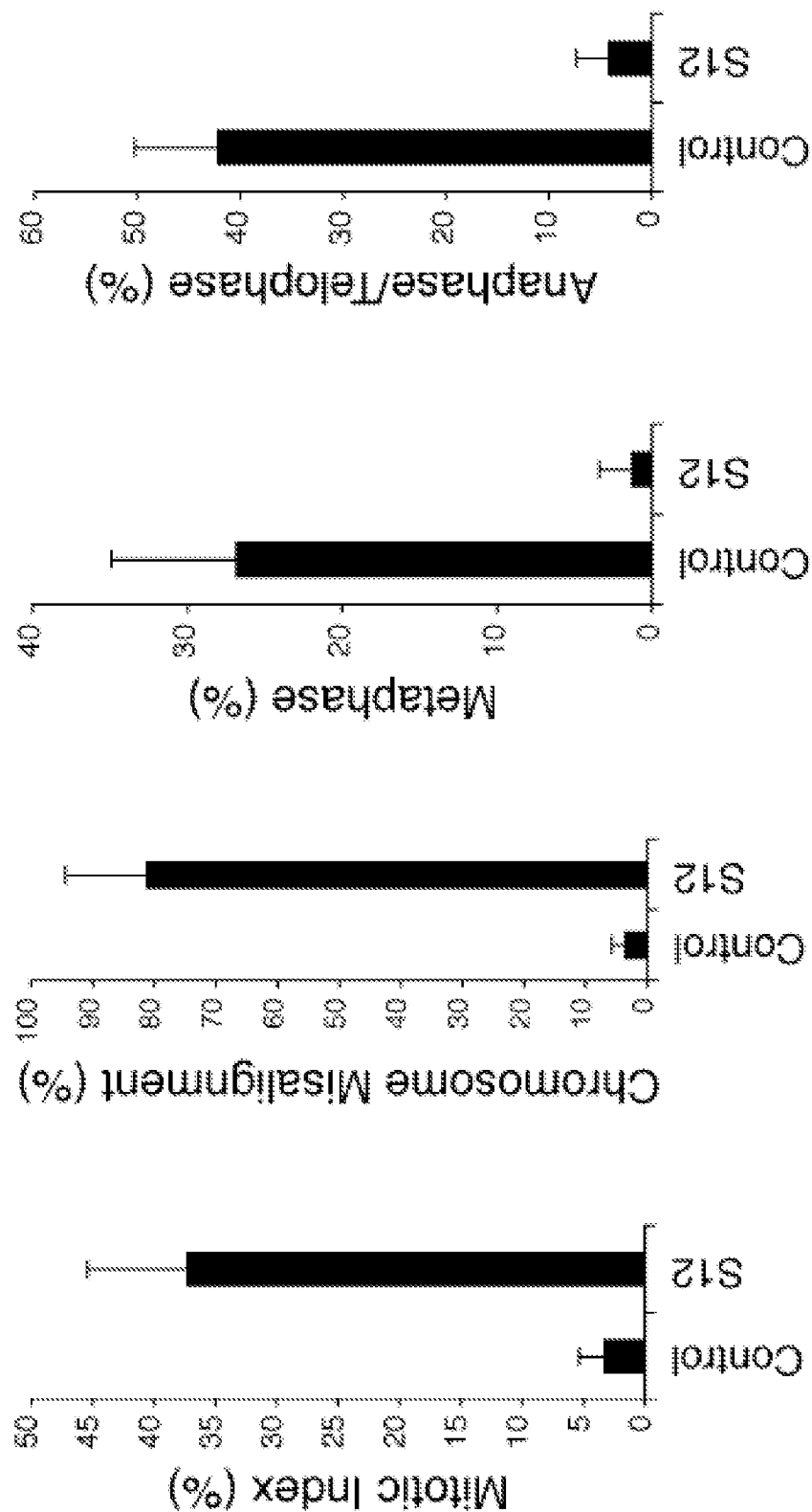
Figure 9:
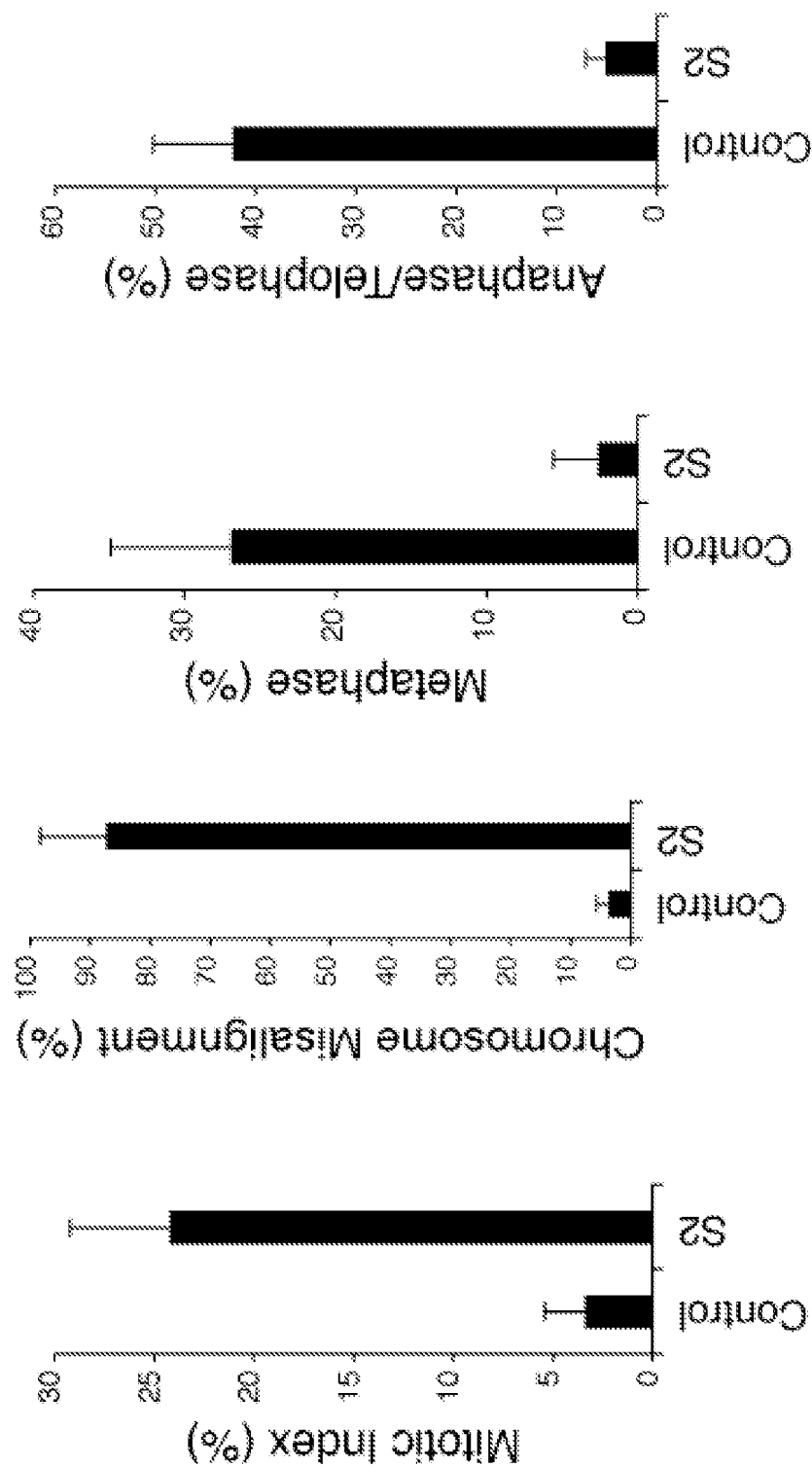
Figure 9D:
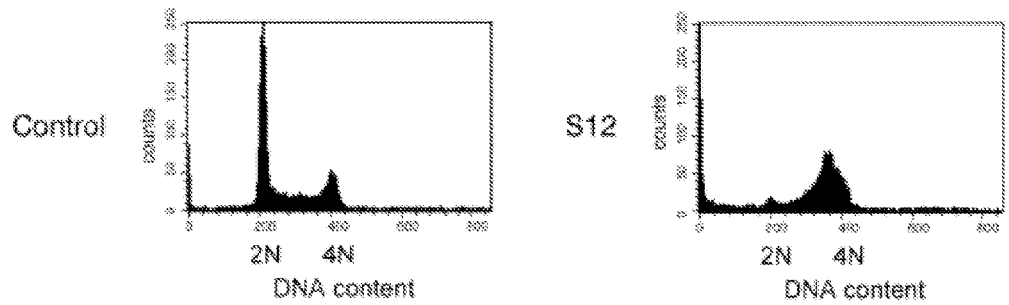

4. S2 and its Analogs Block Cells in Mitosis and Disrupt Mitotic Spindle Formation The candidate Survivin-targeting molecules identified by the virtual screen were examined for the ability to inhibit cell proliferation and mitosis. HeLa cells were treated with the compounds at various concentrations for 15 hours followed by examination of the DNA content by FACS analysis. We found that one of the compounds, designated S2, led to accumulation of cells in the G2/M stage of the cell cycle (FIG. 7). In addition, we observed an increase of cells in the sub-G1 population, which is indicative of cell death. In addition to HeLa cells, S2 also caused G2/M arrest in a variety of other cell lines, such as U87 cells, Jurkat, Raji and Daudi cells. The effects of S2 inflicted on cell proliferation and viability are consistent with the anticipated outcome caused by the ablation of Survivin functions. We have extended these studies to test a number of molecules that are structurally similar to S2, including S10, S11, S12 and S13. As expected, these S2 analogs also exhibit the ability to arrest the cells at the G2/M stage. We found that S12 led to accumulation of cells in the G2/M stage of the cell cycle (FIG. 9). In addition, we observed an increase of cells in the sub-G1 population, which is indicative of cell death. S12 affected cell proliferation and viability, consistent with the anticipated outcome caused by ablation of Survivin functions.

Figure 8:
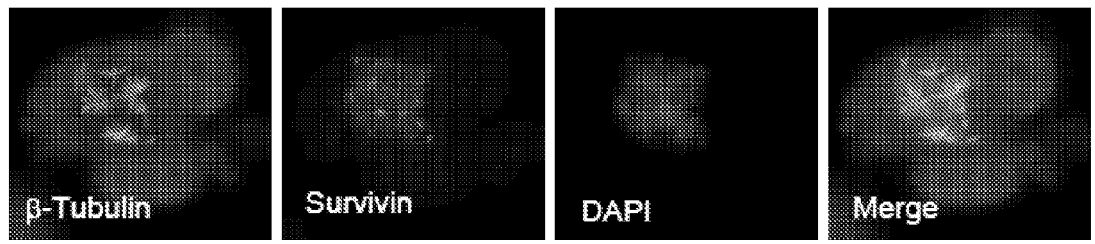
FIG. 8 illustrates the effect of S2 on mitotic spindle formation. HeLa cells were treated with S2 or DMSO for 15 hours. The cells were then fixed and subjected to immunostaining using the anti-β-Tubulin (green) and the anti-Survivin (red). Representative fluorescent microscopy images are shown. Note that short microtubule bundles form in S2-treated cells.

The effect of S2 and its analogs on the progression of cell cycle was examined by immunofluorescence microscopy. HeLa cells were plated on coverglass and treated with the Survivin-targeting compound S2 (10 μg/ml) or with the solvent DMSO alone for 15 hours. Cells were stained with the anti-β-Tubulin antibody (green) and anti-Survivin antibody (red). S2 can block cell division at the early stage of mitosis (FIG. 8). This phenomenon suggests that the cells are arrested by S2 in the prometaphase of the cell cycle. In addition, we found that, in the presence of S2, multiple aster-like microtubule bundles can form in each mitotic cell. The microtubules in this case are very short, with one end attached to the centrosome and the other end to the kinetochore of the chromosomes (FIG. 8). Based on these observations, we conclude that the compound S2 can cause defects in formation of the mitotic spindle.

We extended the immunofluorescence studies to define the cell stage in the cells that were arrested by S2 or its analogs. Cells were also stained with anti-Aurora B antibody or anti-Survivin antibody in order to determine whether the localization of Survivin or Aurora B proteins are changed by these small molecules. Upon S2 or S12 treatment, we observed that cells accumulate in a stage with condensed chromosomes but without proper alignment of chromosomes on the mitotic plate (FIG. 9). The percentage of cells that progress to metaphase or beyond was reduced by S2 or S12 treatment (FIG. 9). These results indicate that the cells are arrested by S2 or S12 in an early stage of mitosis. However, the Survivin antagonists did not alter the localization of Survivin or Aurora B to the kinetochore (FIG. 9). Moreover, localization of Survivin to the midbody was also not affected.

Effects of the Survivin-targeting compound S12 on cell cycle progression was examined by immunofluorescence microscopy. HeLa cells were plated on coverglass and treated with S12 (40 μM) or with the solvent DMSO alone for 15 hours. Cells were stained with anti-Aurora B antibody or anti-Survivin antibody. Upon S12 treatment, it was observed that cells accumulate in a stage with condensed chromosomes but without proper alignment of chromosomes on the mitotic plate expected at metaphase (FIG. 9E).

Figure 19A:
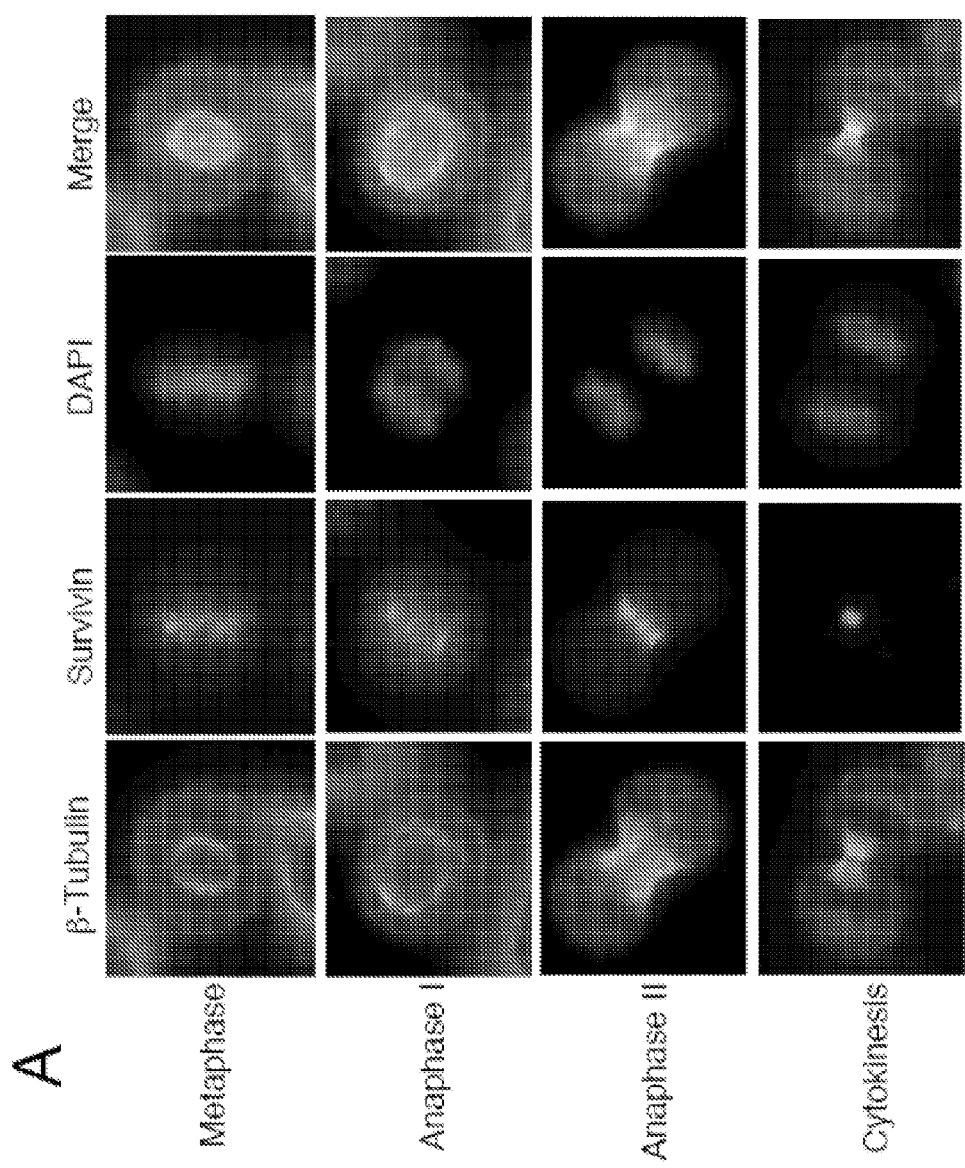
FIG. 19 illustrates immunofluorescence studies of Survivin localization. (A) Untreated HeLa cells were subjected to immunostaining using a monoclonal anti-beta-Tubulin antibody (green) or a polyclonal anti-Survivin antibody (red). Images of cells at various stages of mitosis are shown. (B) HeLa cells were treated with S2 for 6 hours. Cells were immunostained with anti-beta-Tubulin antibody (green) or a polyclonal anti-survivin antibody (red). Note that localization of Survivin to the midbody was not affected by S2.
Figure 19B:
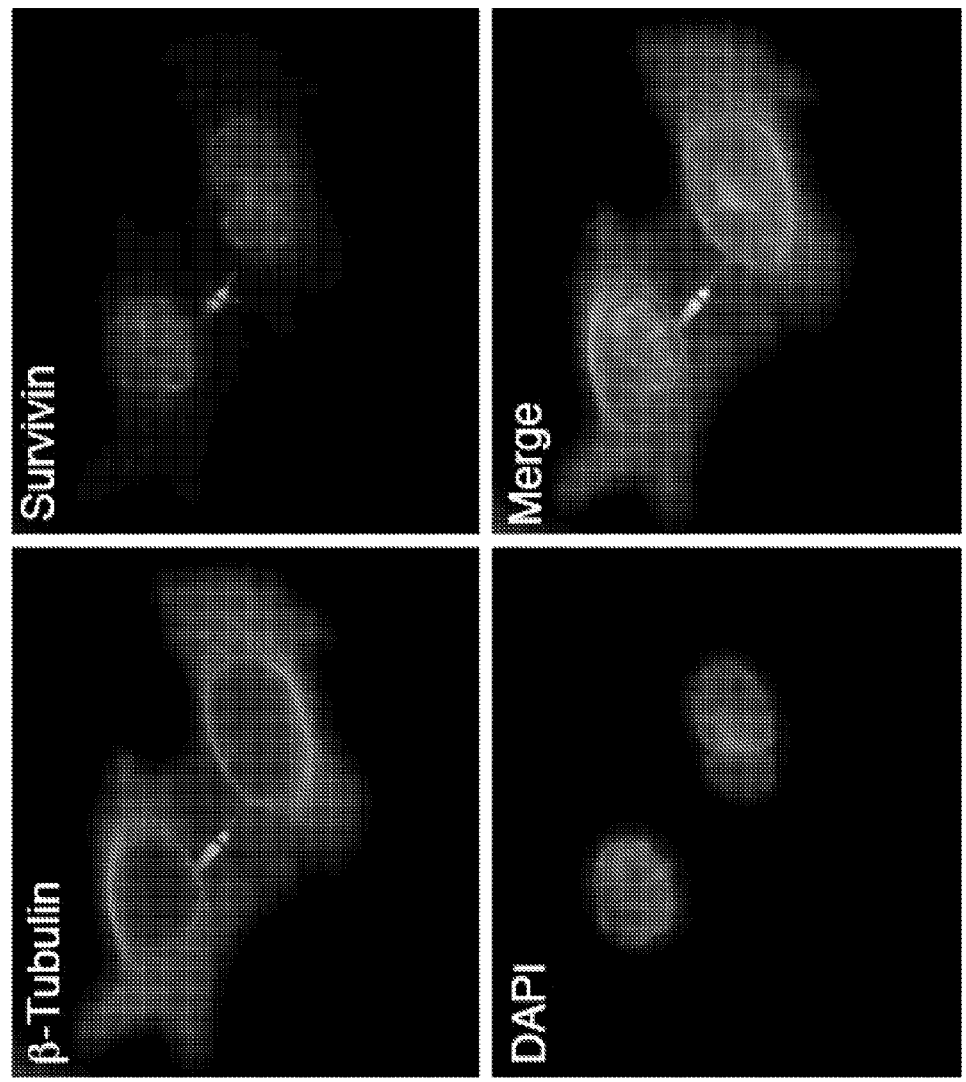

In the presence of the Survivin-targeting compound S12, multiple aster-like microtubule bundles formed in each mitotic cell (FIGS. 19 and 8). These microtubules are typically very short, with one end attached to the centrosome and the other end to the kinetochore of the chromosomes. S12 can cause defects in formation of the mitotic spindle. Cells were arrested by S12 in an early stage of mitosis. However, S12 did not alter the localization of Survivin or Aurora B to the kinetochore (FIG. 9E). Moreover, localization of Survivin to the midbody was also not affected (FIG. 19B). Therefore, the predominant effect is at metaphase related events during mitosis.

5. S2 or S12 Does not Affect DNA Synthesis

Figure 10:
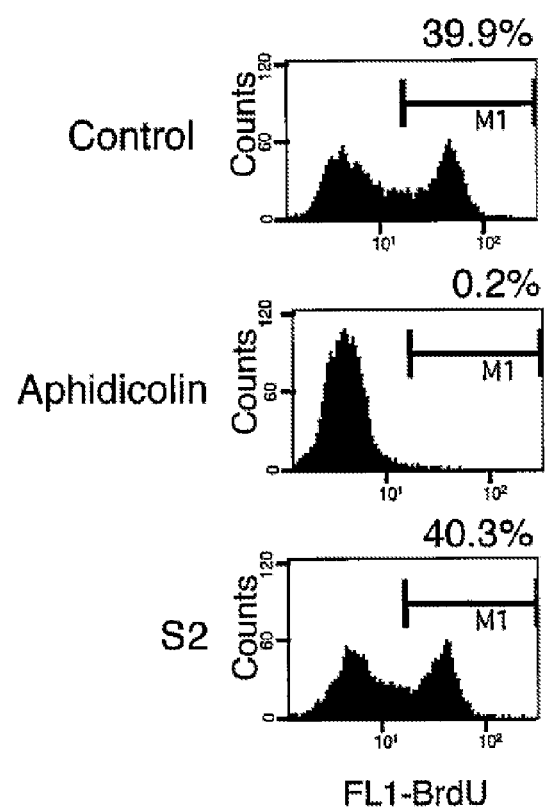
FIG. 10 illustrates that S2 does not affect DNA synthesis. BrdU-labeled cells were analyzed by FACS. The percentage of BrdU-positive cells is indicated.

To establish the specificity of the biological activities of the Survivin targeting we examined whether the compounds affect DNA synthesis. HeLa cells were treated with Aphidicolin, S2 or DMSO for 4 hours, followed by one-hour incubation with BrdU. The cells were then collected, fixed and stained with FITC-labeled anti-BrdU antibody. We found that aphidicolin inhibits DNA replication whereas S2 has no effect on DNA synthesis (FIG. 10). Similarly, S12 also did not block DNA synthesis. These results indicate that S2 or its analogs induce cell death not due to general cytotoxicity but due to their ability to block a specific biological event during mitosis.

Figure 11:
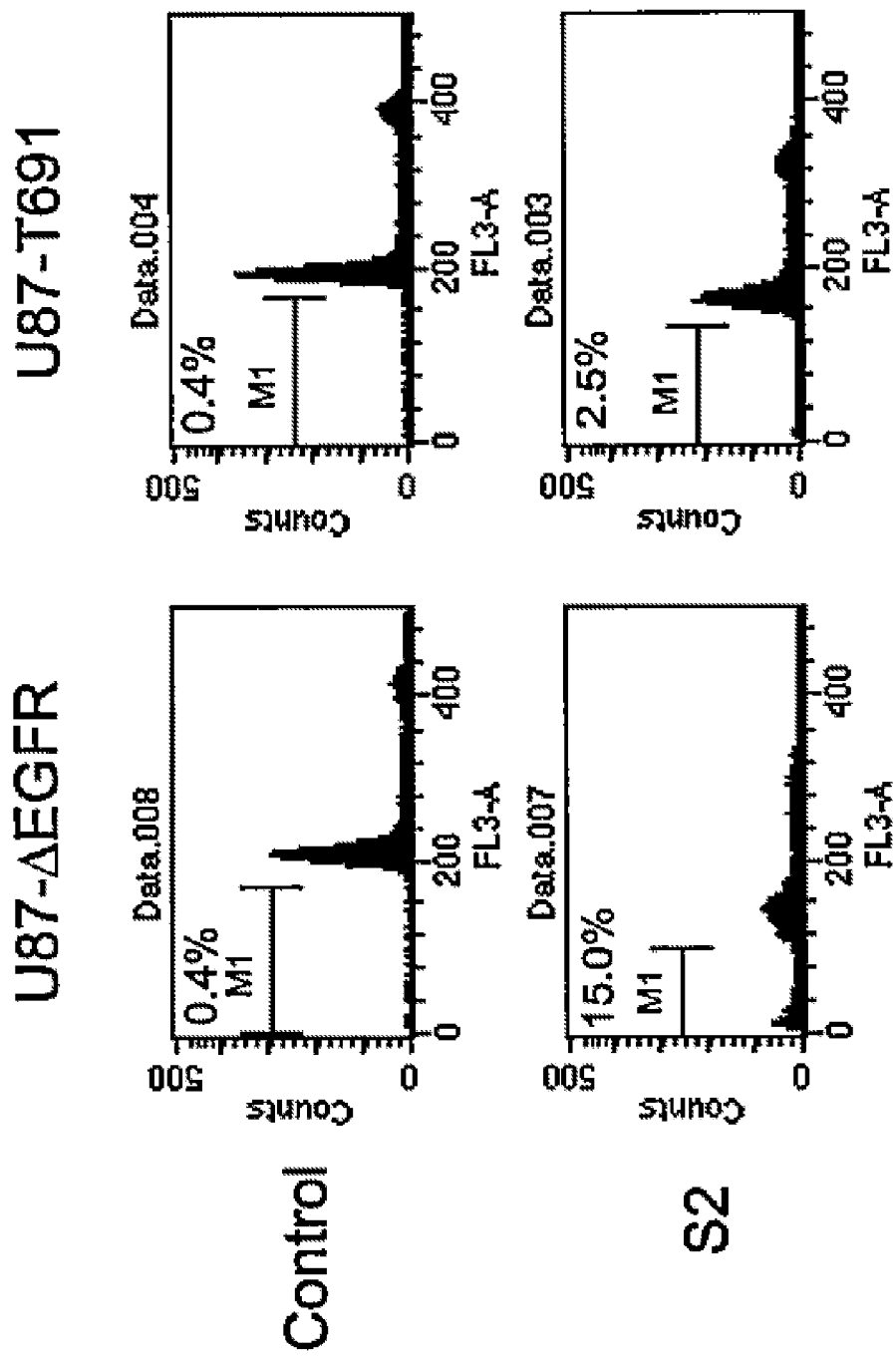
FIG. 11 illustrates the sensitization of Survivin inhibition. U87ΔEGFR and U87-T691 cells were treated with DMSO (control) or S2 at the concentration of 10 μg/ml for 12 hours. Cells were collected and stained for DNA content by propidium iodide (PI) and analyzed by FACS. The percentage of cell death is indicated (sub-G1 population in gate M1). FL3-A: PI staining.

6. Cells with Activated EGFR Signaling are More Sensitive to Treatment of Survivin Targeting Molecules We examined whether Survivin targeting can inhibit cells that have been transfected with an activated form of EGFR. The two cell lines used in the study include (1) U87ΔEGFR cells, which express a constitutively active form of EGFR, and (2) U87T691, which expresses a dominant-negative form of the ErbB receptor (Wang and Greene (2005) EGFR enhances Survivin expression through the phosphoinositide 3 (PI-3) kinase signaling pathway. *Exp Mol Pathol* 79:100-107). Treatment of U87ΔEGFR with S2 at a concentration of 10 μg/ml cause cell death in 12 hours, as reflected by the increase of sub-G1 population of cells in FACS analysis of DNA content (FIG. 11). We did not observe an accumulation of cells in the G2/M stage, probably because the cells quickly undergo apoptosis within 12 hours. In contrast, the U87T691 cells were more resistant to S2 treatment (FIG. 10). Thus, these results indicate that cells with activated EGFR signaling are more sensitive to the Survivin targeting molecules and we will examine the effects of disabling both ErbB pathways and Survivin ensembles in transformed cells.

7. S12 Induces Caspase Activation

We examined whether S12 treatment leads to apoptosis. HeLa cells were incubated with S12 at the concentration of 50 μg/ml or with DMSO alone for 12 hours. To compare the effect with that of other therapeutic agents, HeLa cells were also treated with Taxol, nocodazole, or etoposide, respectively. The cell lysates were collected and subjected to Western blot analysis using an anti-PARP antibody. As shown in FIG. 12, cleavage of PARP, a hallmark of caspase activation, was also detected following S12 treatment. Indeed, at the concentrations we employed, S12 was more potent in inducing apoptosis than Taxol, nocodazole, or etoposide. We also re-probed the blot with an anti-Survivin antibody. S12 did not significantly affect the overall Survivin levels (FIG. 12). These observations, combined with the earlier findings, indicate that the Survivin-targeting molecule S12 can block mitosis and cause apoptosis.

8. S12 Inhibits Tumor Growth In Vivo

Figure 13A:
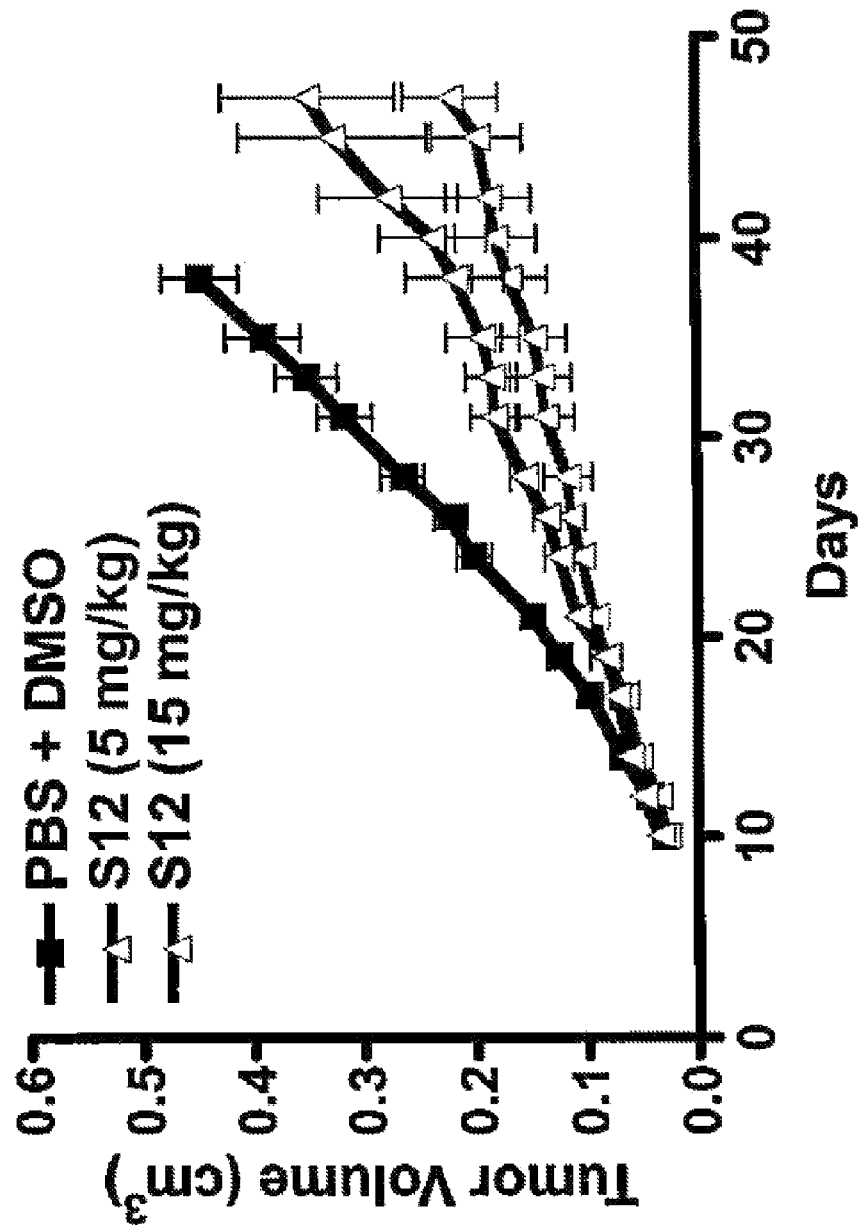
FIG. 13 illustrates S12 inhibition of tumor growth in vivo. (A) AsPC1 cells were injected subcutaneously into the mid-dorsum of athymic mice. S12 was administered 10 days after the injection at the concentration of 5 mg/kg (blue triangles; middle line on the graph, n=4) or 15 mg/kg (red triangles; lower line on the graph; n=3). The control group was treated with PBS containing DMSO only (black square; upper line on the graph). The results represent the mean tumor volume+/− standard error (P<0.05). (B) In a second set of studies S12 was administered at the concentration of 15 mg/kg or 50 mg/kg (n=3). In both studies the control group was treated with PBS containing DMSO only. The results represented the mean tumor volume+/− standard error.

The effect of S12 on tumor growth was examined using a mouse xenograft model. The human pancreatic cell line AsPC1 was injected subcutaneously into athymic mice and formed palpable tumors within 10 days. S12 was then administered at the concentration of 5 mg/kg or 15 mg/kg three times per week until the end point of the experiment. The size of the tumors was monitored for up to 48 days after the initial grafting. Our results indicate that S12 treatment significantly lowered the tumor volume in a dose-dependent manner (FIG. 13A).

Figure 13B:
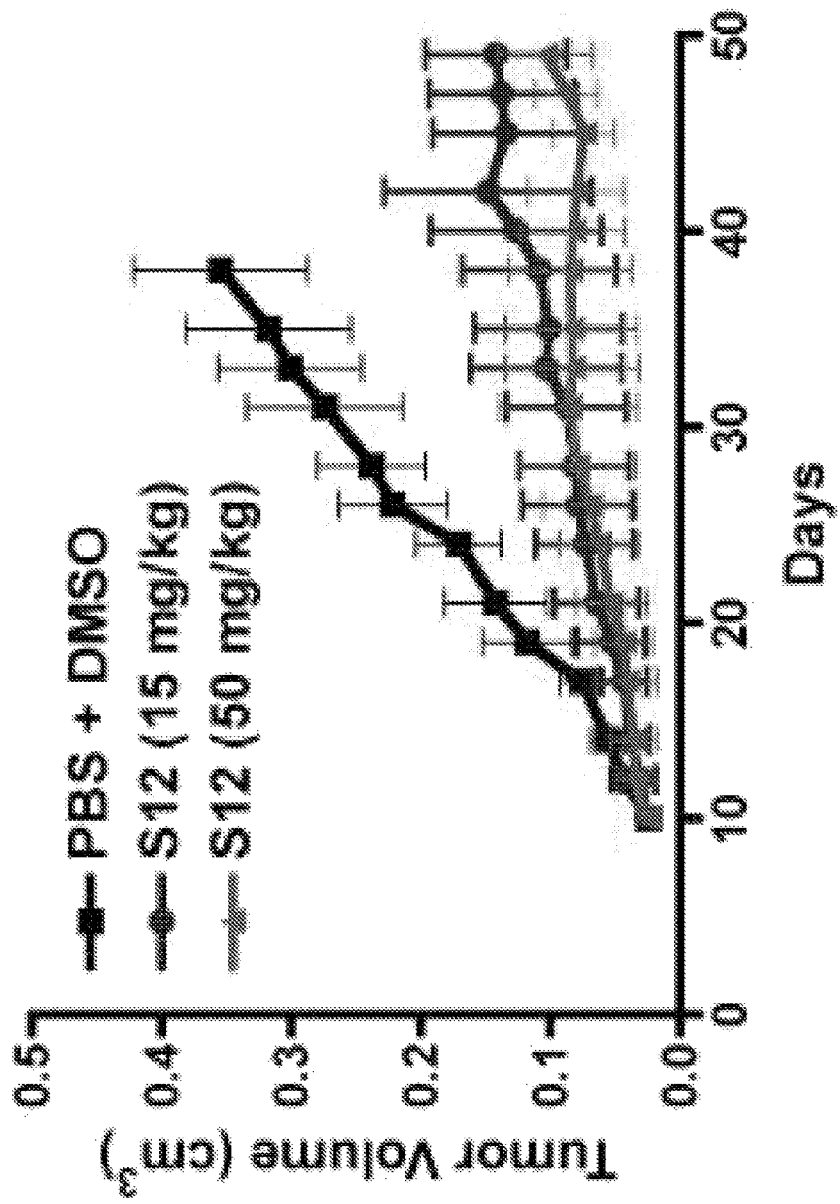

In a separate set of studies, we raised the dose of S12 to 50 mg/kg and observed enhancement of tumor regression. (FIG. 13B). In all these studies, we observed no overtly toxic effects to the mice.

Figure 14:
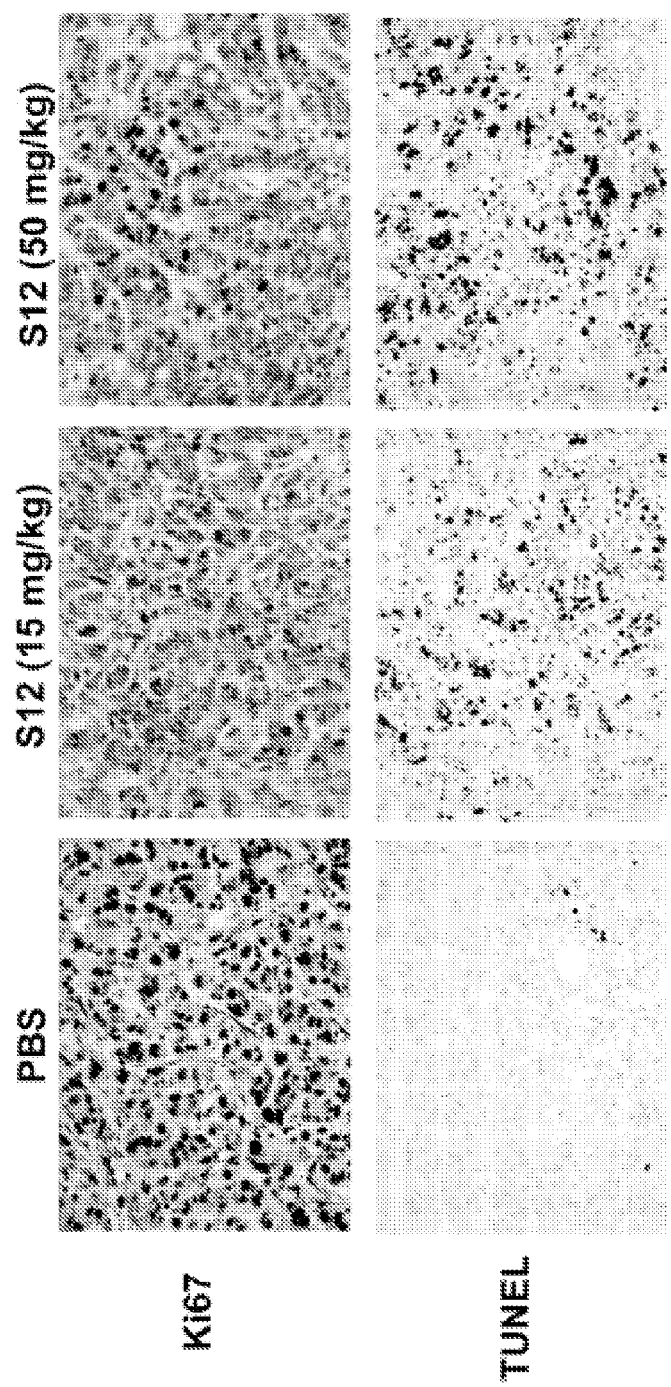
FIG. 14 illustrates the immunohistochemistry analysis of tumor xenograft following treatment with S12 or PBS.
Figure 15:
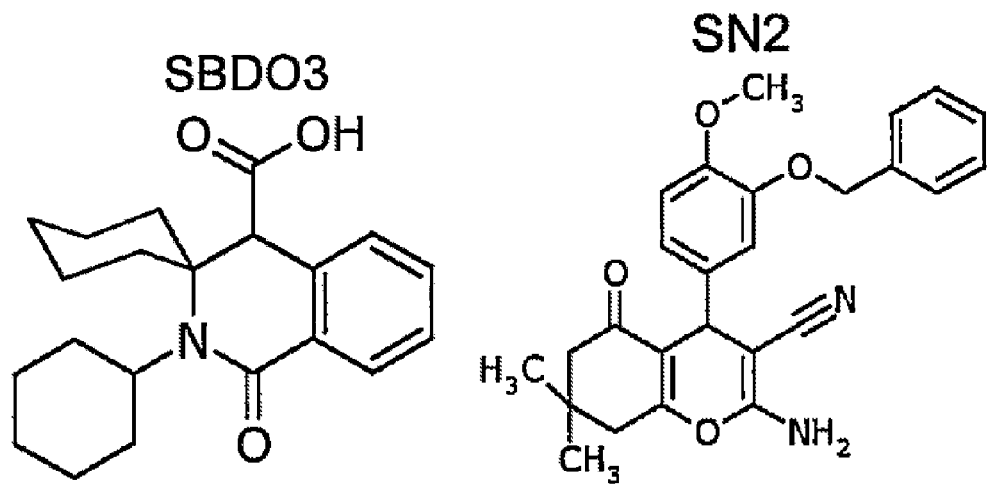
FIG. 15 illustrates molecular structures of the pseudo-allosteric inhibitors of Survivin SBDO3, SN2 and SDC1.
Figure 15:
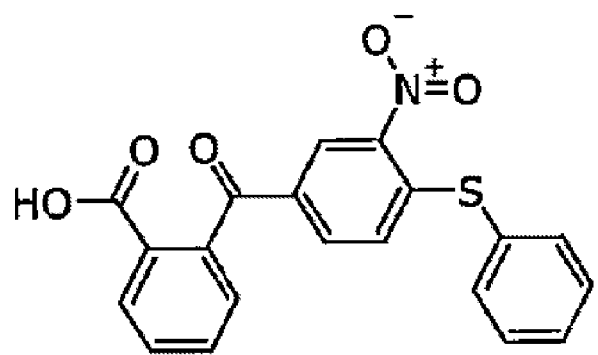

We performed immunohistochemistry studies to analyze the cellular effects of S12 treatment on the tumors. Using Ki67 as a marker for cell proliferation, we found that S12 drastically reduced proliferation of tumor cells (FIG. 14). In addition, we examined apoptosis using the TUNEL assay. Consistent with the findings of the in vitro studies, S12 treatment increased the levels of apoptosis in the tumors (FIG. 14).

9. Binding of SBDO3 and SDC1 to Survivin

Figure 16:
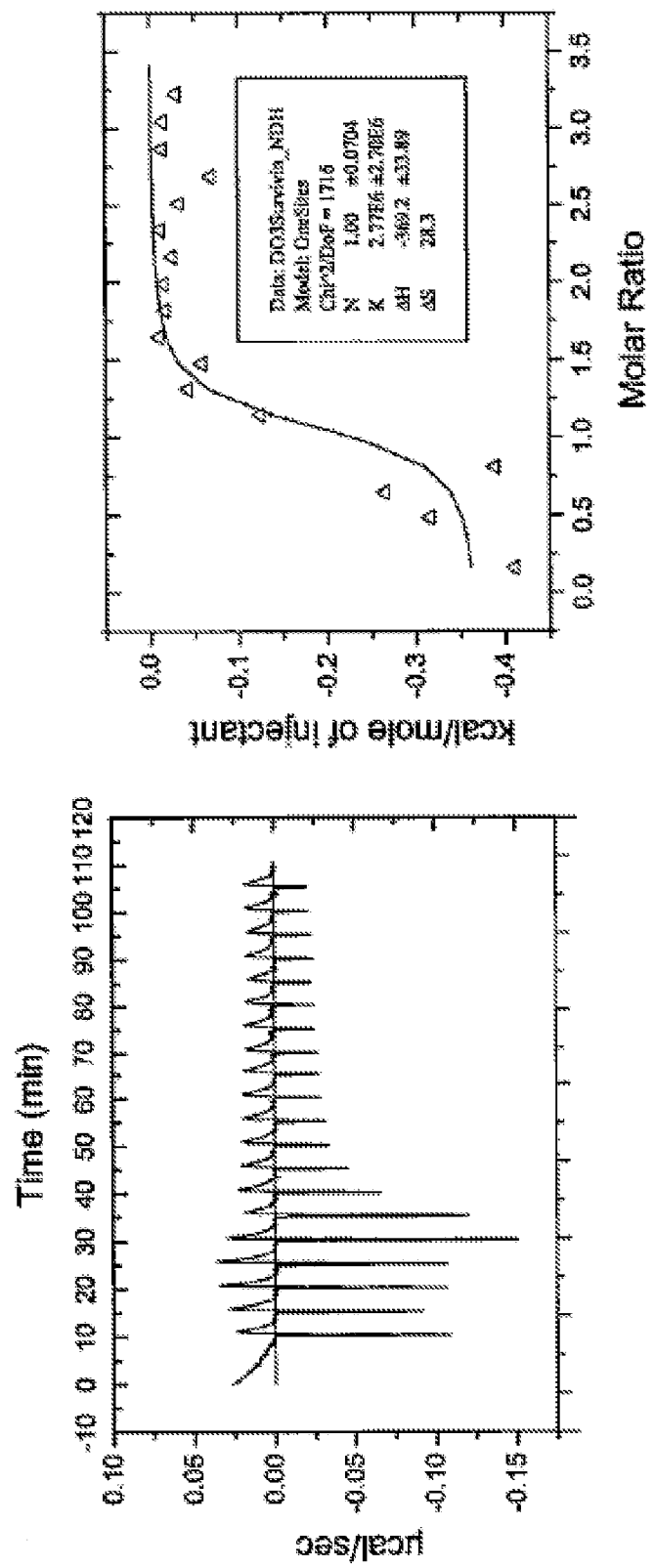
FIG. 16 illustrates the isothermal titration calorimetry profile of the binding of SBDO3 to the Survivin homodimer.

We tested the binding of the Survivin target molecules to Survivin by isothermal titration calorimetry. SBDO3 can bind to Survivin with a deduced stoichiometry of 1:1 (N=1.0; $K=2.8\pm2.7.10^6 M^{-1}$)(FIG. 16). SDC1 also exhibits a similar ITC profile. These results indicate that both SBDO3 and SDC1 can bind to the Survivin protein.

Figure 17:
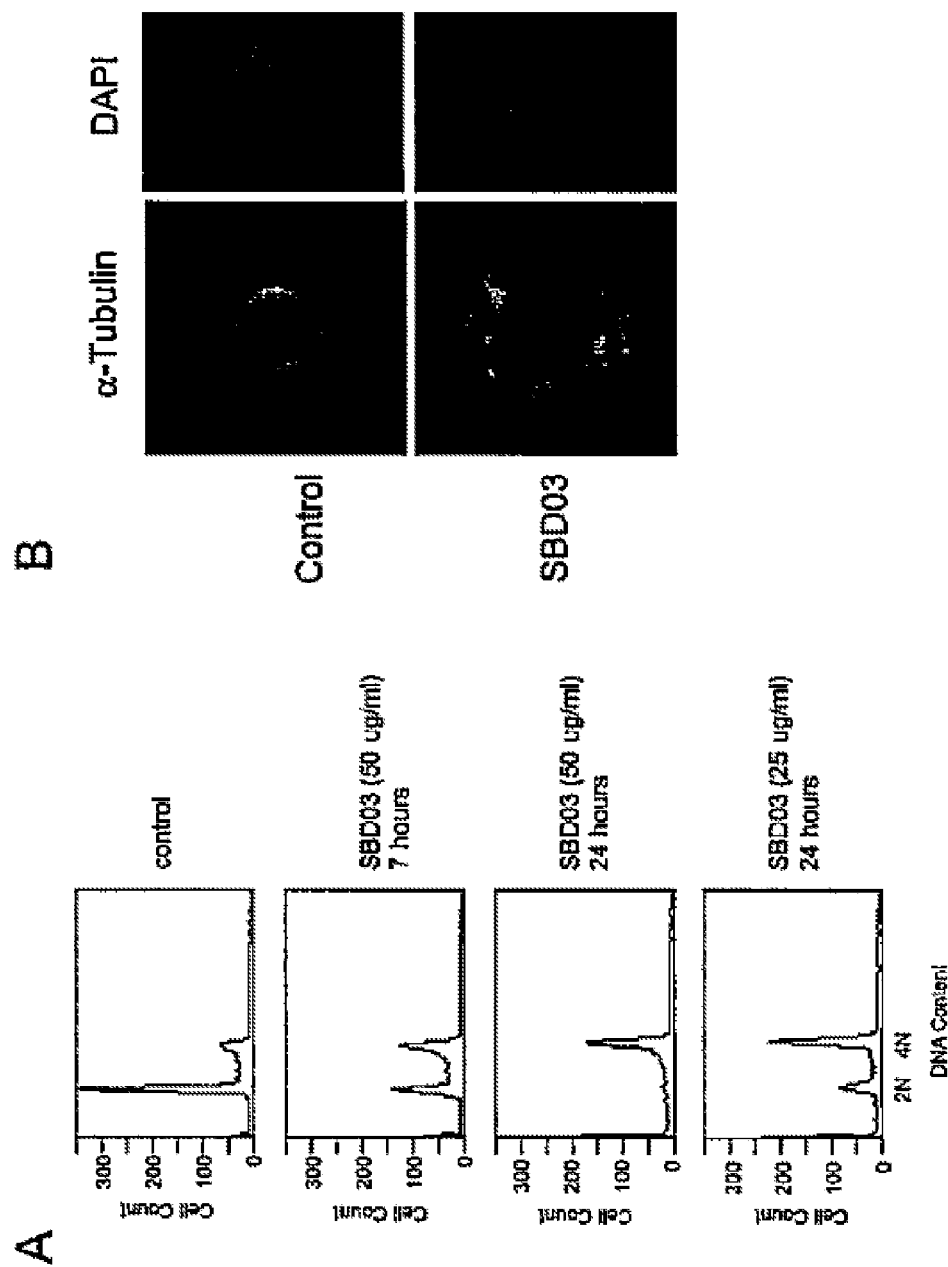
FIG. 17 illustrates (A) FACS analysis of DNA content of HeLa cells treated with SBDO3. Note the accumulation of cells at the G2/M stage. Cell death was also observed (sub-G1 population); (B) Immuno-fluorescence microscopy analysis of cell treated with SBDO3. Note that the microtubule bundles of the mitotic spindle are disorganized. The chromosomes are not aligned properly and cells cannot go through metaphase.

10. Survivin Targeting Compounds SBDO3, SDC1 and SN2 can Arrest Cells in Mitosis We analyzed distribution of cells in the different stages of the cell cycle by FACS. We found that SBDO3 (FIG. 17A) caused accumulation of cells in the G2/M stage. This process was accompanied with increase of cells in the sub-G1 population, which represents dead and dying cells. In addition, the inhibitory effect of SBDO3 is dose dependent (FIG. 17A).

We also conducted immuno-fluorescence studies on SBDO3 treated HeLa cells. Our results verified that SBDO3 can also cause accumulation of cells in early prometaphase and metaphase (FIG. 17B). Similar to S2 and its analogs, SBDO3 caused abnormal formation of the mitotic spindle (FIG. 17B). In addition, the FACS analysis and immunofluorescence studies showed that SDC1 and SN2 can also block cells in mitosis.

11. Inhibition of Tumor Cell Proliferation by SBDO3, SN2 and SDC1

Figure 18:
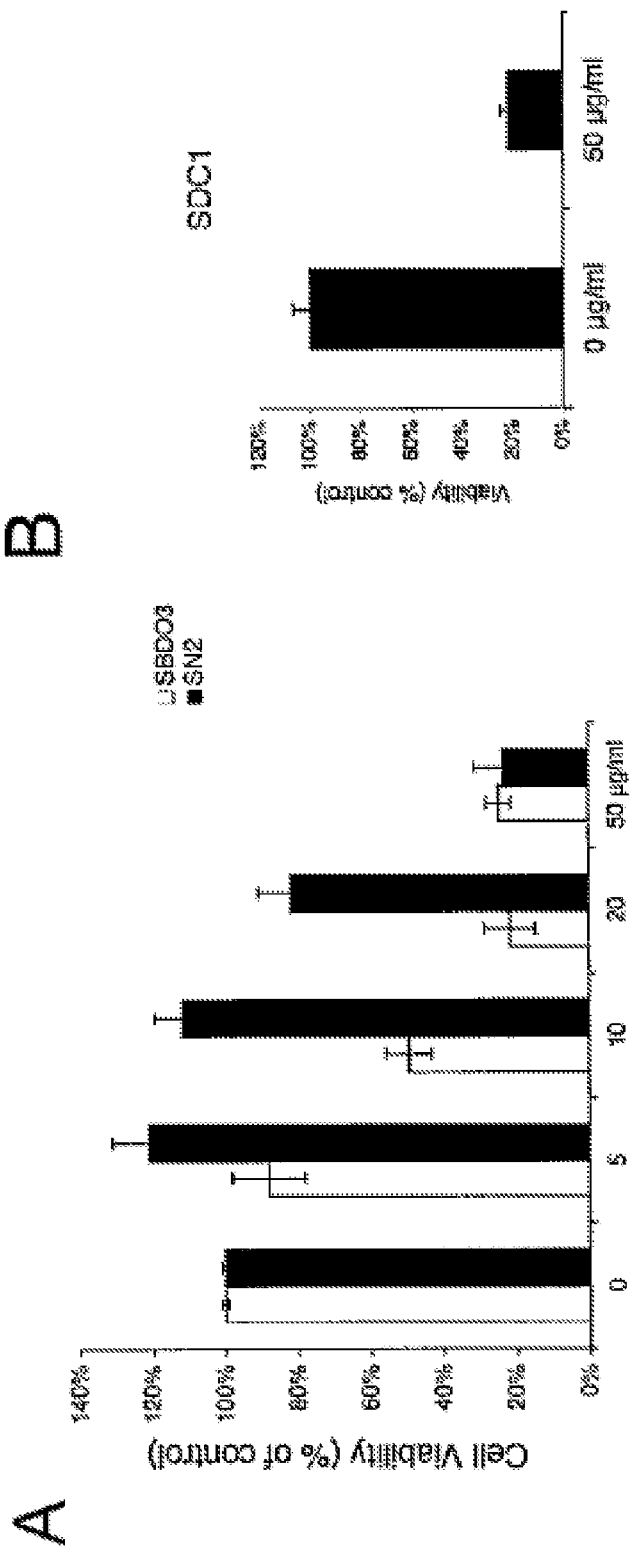
FIG. 18 illustrates the effect of SBDO3, SN2, or SDC1 on tumor cell proliferation. (A) AsPC1 cells were treated with DMSO or the Survivin targeting molecules SBDO3 or SN2 at the indicated concentration for 48 hours. (B) SKBR3 cells were treated with DMSO or SDC1 for 48 hours. The percentage of viable cells was evaluated by MTT assay.

SBDO3, SN2 and SDC1 were tested for the ability to inhibit tumor cell proliferation by MTT assay. The AsPC1 pancreatic cancer cells were treated with DMSO or the Survivin-targeting compounds at the concentration of 5, 10, 20, or 50 µg/ml for 48 hours. The number of viable cells was evaluated by MTT. The data show that the Survivin-targeting compounds can inhibit cell proliferation and reduce cell viability in a dose-dependent manner (FIG. 18A). In addition, the Survivin antagonist SDC1 can inhibit proliferation of SKBR3 breast cancer cell (FIG. 18B).

When ranges are used herein for physical properties, such as molecular weight, or chemical properties, such as chemical formulae, all combinations and subcombinations of ranges specific embodiments therein are intended to be included.

The disclosures of each patent, patent application and publication cited or described in this document are hereby incorporated herein by reference, in their entireties.

Those skilled in the art will appreciate that numerous changes and modifications can be made to the preferred embodiments of the invention and that such changes and modifications can be made without departing from the spirit of the invention. It is, therefore, intended that the appended claims cover all such equivalent variations as fall within the true spirit and scope of the invention.

12. S12 Does not Cause Death of Non-Proliferating S Phase-Arrested Cells

Figure 12B:
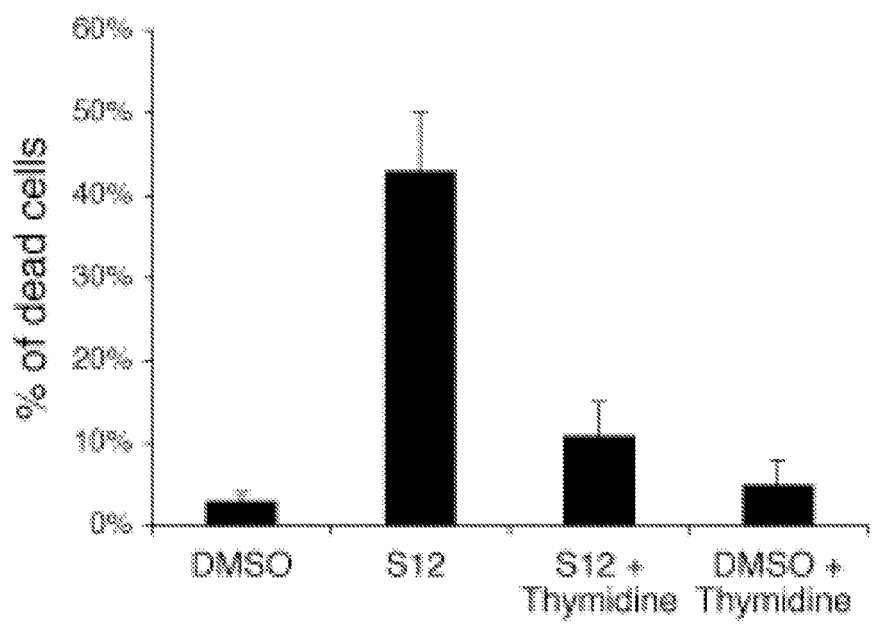
FIG. 12 illustrates S12 induction of caspase activation in HeLa cells. (A) HeLa cells were incubated with DMSO (control), S12, Taxol, nocodazole (Noco), or etoposide (Etop) for 12 hours. The cell lysates were analyzed by Western blot using the anti-PARP antibody (top panel), the anti-α-tubulin antibody (middle panel), or the anti-Survivin antibody (bottom panel). (B) S12 causes cell death in a cell cycle dependent manner. HeLa cells, either unsynchronized or synchronized by thymidine treatment were incubated either with S12 or DMSO. Cell death was quantitated by trypan blue exclusion assay.
Figure 20:
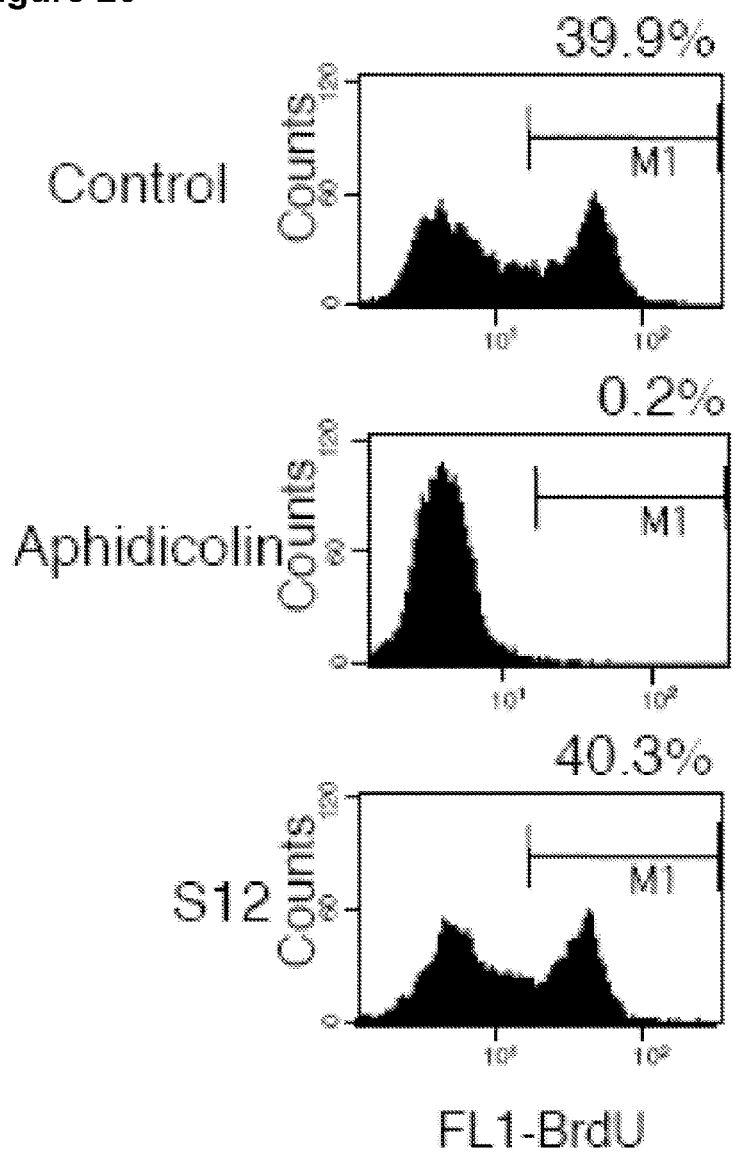
FIG. 20 illustrates that the survivin-targeting compound S12 does not affect DNA synthesis. HeLa cells were treated with S12, aphidicolin, or DMSO (control) for 4 hours. BrdU was then added to the medium followed by an additional incubation of 1 hour. The amount of BrdU was examined by staining with anti-BrdU antibody and FACS analysis. The percentage of BrdU-positive cells is shown.

We wanted to determine if the Survivin-targeting compounds induce cell death during mitosis but could not affect the phenotype or influence in other stages of the cell cycle. To this end, we blocked HeLa cells in the S phase by thymidine treatment and examined whether the cells were susceptible to cell death induced by S12. Our results show that when the cells were arrested in S phase, they were insensitive to S12 (FIG. 12B). In contrast, unsynchronized cells underwent apoptosis in the presence of the Survivin-targeting compound (FIG. 12B). Moreover, S12 did not affect DNA synthesis (FIG. 20), which substantiates that the effect of the Survivin-targeting molecule is restricted to mitosis. Thus, the current data support the notion that S12 induced death of cells is a consequence of mitotic arrest rather than general cytotoxicity and indicate a unique cell cycle specific functionality of Survivin in this process.

What is claimed:

1. A method of treating cancer having Survivin activity comprising administering to a patient in need thereof a small molecule inhibitor of Survivin activity, wherein said small molecule inhibitor of Survivin activity is a compound of formula I or a pharmaceutical acceptable salt thereof

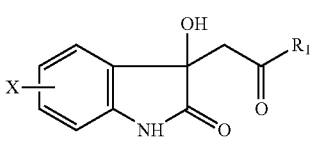
(I)

wherein
X is hydrogen, halogen, —OH, alkoxy, or $C_1$-$C_4$ linear or branched alkyl; and
$R_1$ is $C_1$-$C_6$ linear or branched alkyl or cycloalkyl or $C_6$-$C_{14}$ aryl optionally substituted with halogen, nitro, amine or dioxole.

2. The method of claim 1, wherein the compound of formula I is:

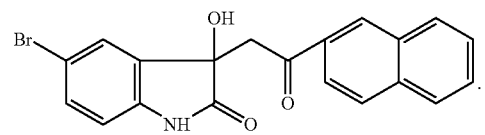 [SMILES: O=C(CC1(O)C(=O)Nc2ccc(Br)cc21)c1ccc2ccccc2c1]

3. The method of claim 1, wherein the compound of formula I is:

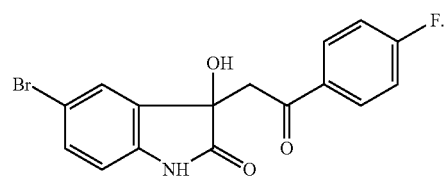 [SMILES: O=C(CC1(O)C(=O)Nc2ccc(Br)cc21)c1ccc(F)cc1]

4. The method of claim 1, wherein the compound of formula I is:

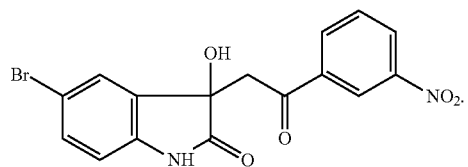 [SMILES: O=C(CC1(O)C(=O)Nc2ccc(Br)cc21)c1cccc([N+](=O)[O-])c1]

5. The method of claim 1, wherein the compound of formula I is:

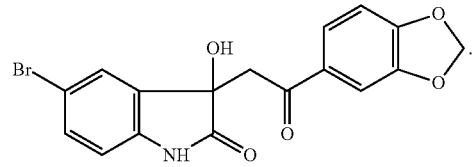 [SMILES: O=C(CC1(O)C(=O)Nc2ccc(Br)cc21)c1ccc2c(c1)OCO2]

6. The method of claim 1, wherein the compound of formula I is:

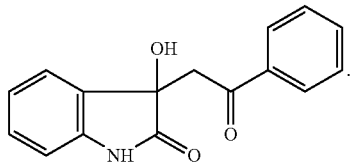 [SMILES: O=C(CC1(O)C(=O)Nc2ccccc21)c1ccccc1]

7. The method of claim 1, wherein the cancer comprises breast, pancreatic, colon, cervical, or lung cancer, or leukemia or tumor metastases.

8. The method of claim 1 wherein the patient is a human.

9. The method of claim 1 further comprising administering to said patient one or more additional anti-cancer agents.

10. The method according to claim 9, wherein said cancer comprises leukemia, breast cancer, brain cancer, colon cancer, lung cancer, cervical cancer or pancreatic cancer.

11. The method according to claim 1, wherein said compound is administered in an amount sufficient to inhibit Survivin activity in said patient.

12. The method according to claim 1, wherein said compound is administered as part of a composition further comprising a physiological acceptable carrier, diluent, excipient, or auxiliary.

13. The method according to claim 12, where the composition is adapted for oral ingestion in the form of a tablet, pill, dragee, capsule, liquid gel, syrup, slurry, or suspension.

* * * * *

UNITED STATES PATENT AND TRADEMARK OFFICE
CERTIFICATE OF CORRECTION

PATENT NO.        : 8,710,068 B2
APPLICATION NO.   : 13/142731
DATED             : April 29, 2014
INVENTOR(S)       : Berezov et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 218 days.

Signed and Sealed this
Twenty-ninth Day of September, 2015

Michelle K. Lee
*Director of the United States Patent and Trademark Office*